United States Patent [19]
Hu et al.

[11] Patent Number: 6,156,570
[45] Date of Patent: Dec. 5, 2000

[54] PROCESS FOR THE CONTINUOUS CULTURE OF CELLS

[75] Inventors: Wei-Shou Hu, Falcon Heights; Anna F. Europa, Minneapolis, both of Minn.

[73] Assignee: Regents of the University of Minnesota, Minneapolis, Minn.

[21] Appl. No.: 09/101,477

[22] PCT Filed: Mar. 19, 1998

[86] PCT No.: PCT/US98/05398

§ 371 Date: Jul. 10, 1998

§ 102(e) Date: Jul. 10, 1998

[87] PCT Pub. No.: WO98/41611

PCT Pub. Date: Sep. 24, 1998

Related U.S. Application Data

[60] Provisional application No. 60/041,162, Mar. 20, 1997, abandoned.

[51] Int. Cl.$^7$ ..................................................... C12N 5/00
[52] U.S. Cl. ........................ 435/375; 435/71.1; 435/139; 435/289.1; 435/325; 435/383
[58] Field of Search .................................. 435/325, 375, 435/383, 289.1, 71.1, 139

[56] References Cited

U.S. PATENT DOCUMENTS 5,443,968  8/1995  Takazawa et al. .

FOREIGN PATENT DOCUMENTS 0387840  3/1990  European Pat. Off. .

OTHER PUBLICATIONS

Bibila et al., "Monoclonal Antibody Process Development Using Medium Concentrates," *Biotechnol. Prog.*, 10, 87–96 (1994).

Carlsen et al., "Growth and α–amylase production by *Aspergillus oryzae* during continuous cultivations," *Journal of Biotechnology*, 45, 81–93 (1996).

Europa et al., "Multiple Steady States in Continuous Cultivation of Animal Cells," Fourth Asia–Pacific Biochemical Engineering Conference, Beijing, China, Oct. 20–23 (1997) (Abstract and Poster (10 pp.)).

Europa et al., "High Density Continuous Culture of Hybridoma Cells," 1997 National AIChE Meeting, Los Angeles, CA, Nov. 16–21 (1997) (Poster only (13 pp.)).

Gambhir et al., "A Strategy for High Cell Density in Continuous Culture of Hybridoma Cells," *Abstracts of Papers, American Chemical Society*, 213$^{th}$ ACS National Meeting, San Francisco, CA, Apr. 13–17 (1997) (Abstract No. 130).

Häggström et al., "Metabolic Engineering of Animal Cells," *Annals of the New York Academy of Sciences*, 782, 40–52 (1996).

Hosobuchi et al., "Dynamic Nutrient Feeding in Hybridoma Cell Culture by using a Statistical Analysis," *Abstracts of Papers, American Chemical Society*, 213$^{th}$ ACS National Mtg., San Francisco, CA, Apr. 13–17 (1997) (Abstract No. 103).

Hu et al., "Controlling Mammalian Cell Metabolism in Bioreactors," *J. Microbiol. Biotechnol.*, 8, 8–13 (1998).

Hu et al., "Dynamic Medium Feeding to Manipulate Cell Metabolism in High Density Fed–batch and Continuous Cultures of Mammalian Cells (conference abstract)," *In Vitro*, 33, V–15 (1997).

Hu et al., "Effect of Glucose on the Cultivation of Mammalian Cells," *Dev. Biol. Standard.*, 66, 279–290 (1987).

Hu et al., "Monitoring and Control of Animal Cell Bioreactors: Biochemical Engineering Considerations," *Large Scale Mammalian Cell Culture Technology*, Ed. A.S. Lubinecki, 451–459, Marcel Dekker, Inc., New York, NY (1990).

Hu, "Needs and Challenges in the Quatitative Descriptions of Animal Cell Culture Process," *Abstracts of Papers, American Chemical Society*, 213$^{th}$ ACS National Meeting, San Francisco, CA, Apr. 13–17 (1997) (Abstract No. 060).

Kurokowa et al., "Growth Characteristics in Fed–Batch Culture of Hybridoma Cells with Control of Glucose and Glutamine Concentrations," *Biotechnol. Bioeng.*, 44, 95–103 (1994).

Kurokawa et al., "Kinetic Study of Hybridoma Metabolism and Antibody Production in Continuous Culture Using Serum–Free Medium," *J. Fermentation and Bioeng.*, 76, 128–133 (1993).

Kyung et al., "Enhanced productivity of Protein C by recombinant human cells in automated fed–batch cultures," *Cytotechnology*, 17, 109–115 (1995).

Linz et al., "Stoichiometry, Kinetics, and Regulation of Glucose and Amino Acid Metabolism of a Recombinant BHK Cell Line in Batch and Continuous Cultures," *Biotechnol. Prog.*, 13, 453–463 (1997).

Ljunggren et al., "Catabolic Control of Hybridoma Cells by Glucose and Glutamine Limited Fed Batch Cultures," *Biotechnol. Bioeng.*, 44, 808–818 (1994).

Oh et al., "Interactive Dual Control of Glucose and Glutamine Feeding in Hybridoma Cultivation," *J. Fermentation Bioeng.*, 81, 329–336 (1996).

Pörtner et al., "High density fed–batch cultures for hybridoma cells performed with the aid of a kinetic model," *Bioprocess Engineering*, 15, 117–124 (1996).

Sanfeliu, "Production of Monoclonal Antibodies by In Vitro Hybridoma Cultures in Bioreactors: Analysis of Physiology and Cellular Metabolism (Igg, Fetal Calf Serum)," *Dissertation Abstracts International*, 58/02, 457 (1995) (Abstract only).

Sanfeliu et al., "Analysis of Nutritional Factors and Physical Conditions Affecting Growth and Monoclonal Antibody Production of the Hybridoma KB–26.5 Cell Line," *Biotechnol. Prog.*, 12, 209–216 (1996).

(List continued on next page.)

Primary Examiner—Leon B. Lankford, Jr.
Attorney, Agent, or Firm—Mueting, Raasch & Gebhardt, P.A.

[57] ABSTRACT

A method for cultivating cells is provided effective to adapt the cells to a metabolic state characterized by low lactate production, thus making possible sustained high cell densities in continuous culture.

46 Claims, 15 Drawing Sheets

OTHER PUBLICATIONS

Snay et al., "Effects of Growth Conditions on Carbon Utilization and Organic By–Product Formation in *B. subtilis*", *Biotechnology Progress*, 5, 63–69 (1989).

Wang et al., *Fermentation and Enzyme Technology*, p. 79, John Wiley & Sons (1979).

Xie et al., "Fed–Batch Cultivation of Animal Cells Using Different Medium Design Concepts and Feeding Strategies," *Biotechnol. Bioeng.*, 43, 1175–1189 (1994).

Xie et al., "High Cell Density and High Monoclonal Antibody Production Through Medium Design and Rational Control in a Bioreactor," *Biotechnology and Bioengineering*, 51, 725–729 (1996).

Zeng et al., "Improved Understanding of Stoichiometry and Kinetics for a Physiological Control of Animal Cell Culture," *Abstracts of Papers, American Chem. Society*, 213$^{th}$ ACS National Meeting, San Francisco, CA, Apr. 13–17 (1997) (Abstract No. 100).

Zhou et al., "Alteration of mammalian cell metabolism by dynamic nutrient feeding," *Cytotechnology*, 24, 99–108 (1997).

Zhou et al. "On–Line Characterization of a Hybridoma Cell Culture Process," *Biotechnol. Bioeng.*, 44, 170–177 (1994).

Zhou et al., "High Viable Cell Concentration Fed–Batch Cultures of Hybridoma Cells Through On–Line Nutrient Feeding," *Biotechnology and Bioengineering*, 46, 579–587 (1995).

Zhou et al., "Establishment of Stoichiometric Relations and Material Balance in Fed–batch Mammalian Cell Cultures," *Abstracts of Papers—Part 1, American Chemical Society*, 209$^{th}$ ACS Meeting, Anaheim, CA, Apr. 2–6 (1995) (Abstract No. 009).

Zhou et al., "High Viable Cell Concentration Fed–batch Hybridoma Cultures by Controlling Cell Metabolism via Dynamic Nutrient Feeding," *Abstracts of Papers—Part 2, American Chemical Society*, 209$^{th}$ ACS National Meeting, Anaheim, CA, Apr. 2–6 (1995) (Abstract No. 005).

Zhou et al., "Control of Cell Metabolism in High Density Fed–batch Cultures by Dynamic Nutrient Feeding (abstract)," *Cytotechnology*, 14, ESACT/JAACT Meeting (1994) (Program and abstracts).

Zhou et al., "Effect of Insulin on a Serum–Free Hybridoma Culture," *Biotechnol. Bioeng.*, 47, 181–185 (1995).

Zielke et al., "Reciprocal Regulation of Glucose and Glutamine Utilization by Cultured Human Diploid Fibroblasts," *J. Cell. Physiol.*, 95, 41–48 (1978).

|  | Culture without metabolic shift | Culture with metabolic shift Stage 3 as shown in Figure 1 |
|---|---|---|
| $q_{glucose}$ (mmol/$10^9$/hr) | 0.13 | 0.032 |
| $q_{lactate}$ (mmol/$10^9$/hr) | -0.17 | -0.0014 |
| $q_{glutamine}$ (mmol/$10^9$/hr) | 0.065 | 0.018 |
| $q_{ammonia}$ (mmol/$10^9$/hr) | -0.05 | -0.02 |
| Lactate/Glucose (mol/mol) | 1.3 | 0.04 |
| Lactate (mM) | 6.90 | 0.22 |
| Ammonia (mM) | 1.9 | 2.8 |
| Viable Cell ($10^6$/mL) | 1.2 | 5.0 |

Figure 8

PROCESS FOR THE CONTINUOUS CULTURE OF CELLS

This application claims the benefit of U.S. Provisional application Ser. No. 60/041,162, filed Mar. 20, 1997, now abandoned, which is incorporated herein by reference, in its entirety.

BACKGROUND OF THE INVENTION

The past fifteen years witnessed the transformation of animal cell culture from an exploratory protein production method to a mature manufacturing process. This technological transformation was aided by significant advances in bioprocessing research and development. As the technology becomes more mature the pressure on driving the production cost down is mounting.

Mammalian cells are capable of utilizing different proportions of glucose and glutamine and metabolize them differently under different culture conditions. Early work by Zielke et. al. (*J. Cell. Physiol.*, 95, 41–48 (1978) showed that glutamine becomes a predominant source of energy at low glucose concentrations. The metabolism of glucose is also greatly affected by glucose concentration in the medium (W.-S. Hu et al., *Dev. Biol. Standard.*, 66, 279–290 (1987); W.-S. Hu et al. in: *Large Scale Mammalian Cell Culture Technology*, Ed. A. S. Lubineicky, pp. 451–481, Marcel Dekker, Inc., New York, N.Y. (1990)). At high glucose levels, the consumption rate of glucose is higher, although most of the glucose consumed (80–90%) is converted to lactate; at low glucose concentrations, the consumption rate for glucose is lower and a larger proportion is completely oxidized to $CO_2$.

This tendency of mammalian cells to metabolize glucose to lactate greatly restricts the cell concentration achievable in the bioreactor. Accumulation of lactate in the medium is detrimental to cell growth and is one of the factors that limits the maximum cell concentration that can be achieved in batch culture. In a typical batch cell culture, growth is inhibited after lactate concentration in the culture reaches approximately 30–50 mM and/or ammonia concentration reaches 3–5 mM. As a result, cell concentration in a batch culture is typically in the range of 1 to $3 \times 10^6$ cells/ml.

Accumulation of lactate can be reduced by changing from a batch mode into a simple continuous operation, thereby continuously removing the spent culture medium containing lactate and cells. Eventually the concentrations of cells, medium components, and metabolites all stabilize, reaching a steady state. However, using the same medium and resulting steady state cell concentration is, at most, about the same level as that reached in batch mode. Cell concentrations usually cannot be much improved by merely increasing the nutrient concentration in the feed, because an increase in nutrient levels in the feed is generally followed by increased lactate and ammonia production and accumulation, thereby preventing the desired increase in cell concentration.

Perfusion cultures have also been used in attempts to achieve high cell concentrations in a bioreactor, and productivity is significantly higher than in conventional batch cultures. However, the large through-put requirement makes medium preparation for perfusion cultures a daunting task. In a perfusion culture, medium is perfused through the reactor at a high rate while cells are retained or recycled back into the reactor by sedimentation, centrifugation or filtration. Up to ten reactor volumes of medium is perfused through the bioreactor in a day. The major function of perfusing such a large volume of medium is primarily to remove the metabolites, mainly lactate, from the culture fluid. The large demand for medium, the high flow rates, and the multitudinous technical problems associated with cell retention devices make the perfusion cultures expensive, labor-intensive, and prone to technical difficulties.

Attempts have been made to increase cell concentration in fed-batch cultures by controlling glucose and/or glutamine concentrations in an effort to reduce the accumulation of inhibitory metabolites. See, e.g., Kurokowa et al., *Biotechnol. Bioeng.*, 44, 95–103(1994); G.-S. Oh et al., *J. Fermentation Bioeng.*, 81, 319–336 (1996); A. Sanfeliu et al., *Biotechnol. Prog.*, 12, 209–216 (1996); W. Zhou et al., *Biotechnol. Bioeng.*, 46, 579–587 (1995). However, in most cases, growth rates and maximum cell concentration are still limited (e.g., J. Ljunggren et al., *Biotechnol. Bioeng.* 44, 808–818 (1994)), and cell viability in fed-batch cultures is usually rather low.

Cell concentration in large-scale mammalian cell cultures has thus been limited by the heretofore unavoidable accumulation of inhibitory metabolites in the culture medium, and methods to address the problem have been directed to removing inhibitory metabolites, such as lactate and ammonia, from the culture. A different approach, comprising a method for culturing cells that avoids excess production and accumulation of toxic metabolites such as lactate in the first place, would represent a far better solution to this long-standing problem.

SUMMARY OF THE INVENTION

The present invention provided a process for cultivating cells, preferably mammalian cells, that minimizes the accumulation of lactate and, optionally, ammonia in the cell culture. Cells in a fed-batch culture are subjected to growth conditions that cause them to produce low levels of lactate compared to conventional cultures. These cells presumably make use of a different metabolic pathway in metabolizing the carbon source. The metabolically-shifted fed-batch culture is then converted to a continuous culture while maintaining low lactate production during the course of the continuous culture.

Accordingly, the invention provides a method for culturing cells in a suspension state comprising (a) periodically or continuously delivering to a batch cell culture a first nutrient feed solution comprising glucose in a concentration effective to yield a fed-batch cell culture characterized by a molar stoichiometric ratio of lactate produced to glucose consumed which ratio is also referred to at times therein as a lactate to glucose molar stoichiometric ratio, of less than about 1; (b) converting the fed-batch cell culture to a continuous cell culture; and (c) continuously delivering to the continuous cell culture a second nutrient feed solution containing glucose in a concentration effective to maintain a lactate to glucose molar stoichiometric ratio of less than about 1 in the continuous cell culture. The lactate concentration in the fed-batch culture immediately prior to conversion to continuous mode is preferably less than about 80 mM, more preferably less than 30 mM, even more preferably less than about 5 mM, and the lactate concentration in the subsequent continuous culture is preferably less than about 30 mM, more preferably less than about 5 mM, most preferably less than about 1 mM, during period of the continuous culture.

In a conventional cell culture where glucose is provided as the carbon source, lactate is typically the predominant observed metabolite. The sustained, unusually low level of lactate production in the cultures of the present method is strong evidence that the cells have shifted to the use of an alternative metabolic pathway to metabolize glucose. The "metabolic shift" that appears to characterize the present invention is initiated in the fed-batch phase and maintained during the continuous culture. In a preferred embodiment of the present invention, this metabolic shift is initiated and maintained by keeping the glucose concentration and, optionally, the glutamine concentration in the cellular environment low; preferably, the culture environment in the continuous culture contains about 0.05 to about 0.4 mM glucose.

Prior to conversion to continuous mode, the fed-batch culture is characterized by a lactate to glucose molar stoichiometric ratio of less than about 1, and this value is preferably not exceeded during the subsequent continuous culture.

Use of a fed-batch culture facilitates the initial manipulation of cellular metabolism to a physiological state that is very efficient in energy metabolism and results in significantly reduced inhibitory metabolite (e.g., lactate) production compared to that observed in conventional cultures. After the metabolic shift has been effected, and when the cells have attained a sufficiently high concentration, typically at least about 4–5×10$^6$ viable cells/mL, the culture is switched from fed-batch mode into a continuous mode. The cells in the continuous culture typically reach a steady state cell concentration of up to three times that achieved in conventional continuous cultures in which cells are in a less efficient metabolic state. Preferably, the cell density in the continuous culture of the present invention is at least about 5×10$^6$ viable cells/mL. The present method is thus well-suited to use in a continuous bioreactor, and has the potential to drastically reduce the amount of medium used in industrial processing, yielding major cost savings.

BRIEF DESCRIPTION OF THE DRAWINGS

FIG. 8. Comparison of various metabolic parameters in two different steady states.

DETAILED DESCRIPTION

Figure 1:
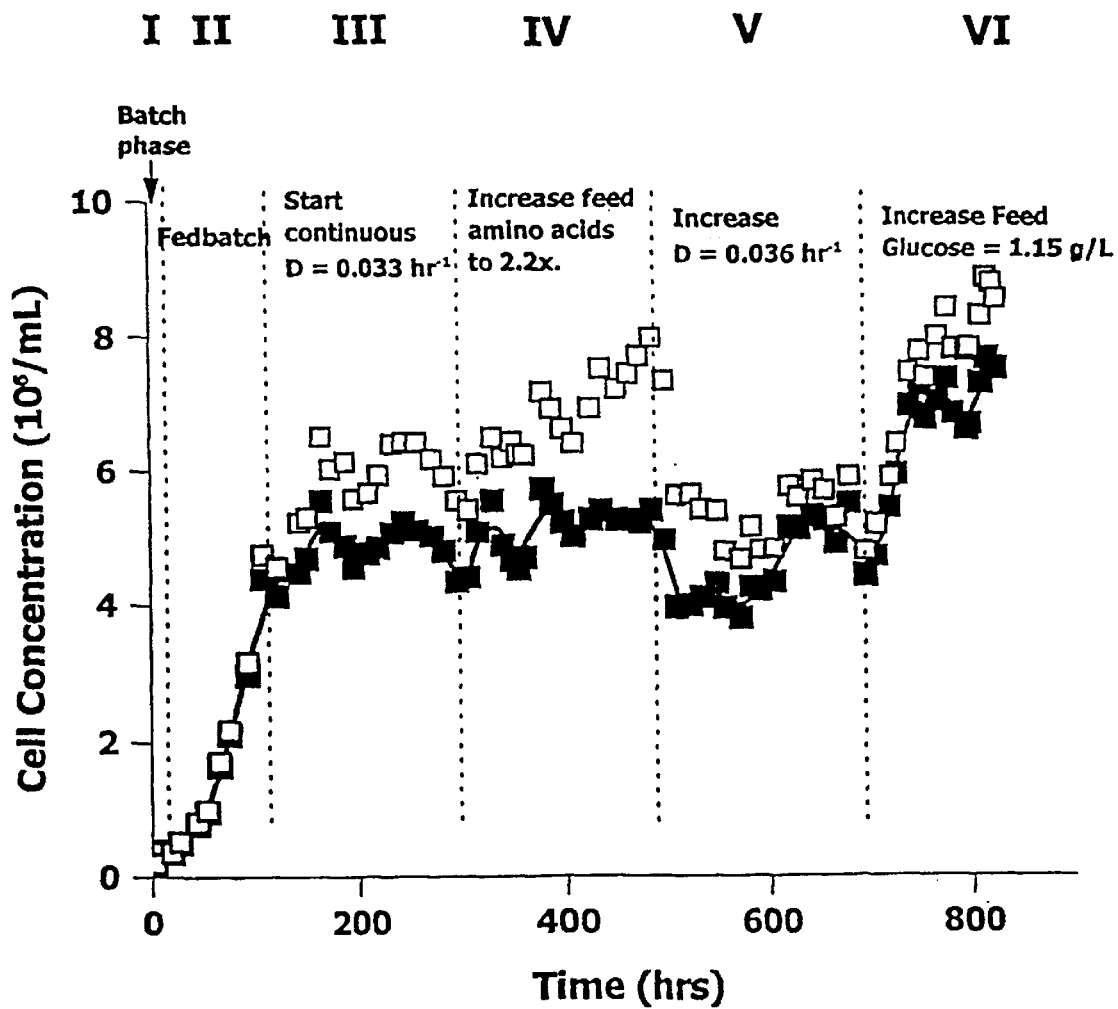
FIG. 1. Viable (filled squares) and total (open squares) cell concentrations versus time in high density continuous culture of hybridoma cells according to the invention. The entire culture is divided into six (6) phases as illustrated.

As used herein, the term "fed-batch" describes a batch cell culture to which substrate, in either solid or concentrated liquid form, is added either periodically or continuously during the run. Just as in a batch culture, a fed-batch culture is initiated by inoculating cells to the medium, but, in contrast to a batch culture, there is a subsequent inflow of nutrients, such as by way of a concentrated nutrient feed. In contrast to a continuous culture there is no systematic removal of culture fluid or cells from a fed-batch culture is advantageous in applications that involve monitoring and manipulating the levels of various analytes in the culture medium, since the concentrations of nutrients and metabolites in culture medium can be readily controlled or affected by altering the composition of the nutrient feed. The nutrient feed delivered to a fed-batch culture is typically a concentrated nutrient solution containing an energy source, e.g., carbohydrates; optionally, the concentrated nutrient solution delivered to a fed-batch culture can contain amino acids, lipid precursors and/or salts. In a fed-batch culture, this nutrient feed is typically rather concentrated to minimize the increase in culture volume while supplying sufficient nutrients for continued cell growth.

The term "continuous cell culture" or, simply, "continuous culture" is used herein to describe a culture characterized by both a continuous inflow of a liquid nutrient feed and a continuous liquid outflow. The nutrient feed may, but need not, be a concentrated nutrient feed. Continuously supplying a nutrient solution at about the same rate that cells are washed out of the reactor by spent medium allows maintenance of a culture in a condition of stable multiplication and growth. In a type of bioreactor known as a chemostat, the cell culture is continuously fed fresh nutrient medium, and spent medium, cells and excreted cell product are continuously drawn off. Alternatively, a continuous culture may constitute a "perfusion culture," in which case the liquid outflow contains culture medium that is substantially free of cells, or substantially lower cell concentration than that in the bioreactor. In a perfusion culture, cells can be retained by, for example, filtration, centrifugation, or sedimentation.

A fed-batch culture is converted to a continuous culture by initiating a substantially continuous inflow of nutrients, which continuous inflow can take the form of a typical cell culture medium or a concentrated nutrient feed, concurrent with a substantially continuous outflow or other systematic removal of culture medium or cells.

Cells cultured according to the present method are typically, but need not be, the product of recombinant DNA technology and can be mammalian or from insect or other animal sources, such as chickens and fish. Preferably, the cells are vertebrate cells, more preferably, mammalian cells. Hybridoma cells, Chinese Hamster Ovary (CHO) cells, Baby Hamster Kidney (BHK) cells, and 293 cells (from human kidney), are particularly well-suited for use in the method of the invention.

The continuous cell culture of the invention has a relatively high viability level. Viability is defined as percentage of cells in the culture that are living. Preferably, viability in the continuous cell culture is more than about 70%, more preferably more than about 80%, most preferably above 90%. In some applications, a viability level of 50% in the continuous culture is suitable.

Cells cultured according to the present method are in a "suspension state." A "suspension" of cells is to be broadly understood as including all types of suspended or dispersed cell cultures; the term "suspension state" is thus used to distinguish cells that are not cultured in a liquid medium, such as cells cultured by way of adhering on a petri dish. Thus, the term "suspension" includes both freely dispersed cells and agglomerated cells, regardless of whether agglomeration occurs spontaneously or as a result of some exogenously supplied nucleating factor or agent.

The present method optionally includes harvesting the cultured cells during or subsequent to the period of continuous culture. Harvesting methods include, but are not limited to, centrifugation, settling, filtration and acoustic separation.

Cells cultured according to the present method can, optionally, produce a product, preferably a protein or virus product, that can be isolated and, optionally, purified for later use. These products can be intracellular or extracellular. Examples include protein pharmaceuticals, antibodies such as IgG and virus for vaccines or for gene therapy. Methods of isolating these products include, but are not limited to, ultrafiltration and chromatography. The present method optionally includes obtaining these products from the cell culture during or after the period of continuous culture.

Cells cultured according to the present method appear to have experienced what is referred to here in a "metabolic shift," i.e., a change in the metabolic pathways used to break down glucose. In conventional cell cultures (i.e., cultures that have not been "metabolically shifted" as described herein) cells are known to utilize both glucose and glutamine as a carbon source, and convert the carbons preferentially to lactate (as opposed to $CO_2$ and the resultant increase in biomass, as described in detail below). This conventional carbon metabolism is typically seen in a batch culture of mammalian cells. In a batch culture the glucose concentration is typically initially at a level of about 5.5 mM to 45 mM. During cell growth, the glucose concentration gradually decreases as glucose is consumed and can reach nearly zero depending on the extent of cell growth. At lower glucose concentrations, however, the cells may begin to convert the bulk of glucose and glutamine consumed to $CO_2$ instead of lactate. In the latter case, where glucose and glutamine are preferentially converted to $CO_2$ in the tricarboxylic acid cycle as opposed to being converted into lactate, nutrient utilization is more efficient, and the yield of biomass increases. The present invention is directed to maintaining the cells in this altered metabolic state during a sustained period of continuous culture.

Unlike glucose, glutamine contains nitrogen. The nitrogen serves as a source for cells to make other amino acids and proteins as well as purines and pyrimidines necessary for nucleic acid synthesis. However, when glutamine consumed is in excess of what is needed for synthesizing other amino acids and proteins, cells excrete the excess nitrogen as ammonia and some non-essential amino acids. It is therefore not desirable to simply increase glutamine concentration in the cell medium as a method for altering carbon metabolism. At low glutamine concentrations, cells take in less "excess" glutamine (i.e., amounts over and above the amount necessary for catabolic processes) and, accordingly, produce less ammonia. It is therefore especially beneficial to control the cell metabolism by decreasing both glucose and glutamine concentrations for reduced lactate and ammonia production.

The fate of carbon during a continuous culture can, under controlled conditions, be influenced or even determined by the initial metabolic state of the cells. Thus, for a given nutrient feed under the same dilution rate in a continuous culture (thereby imposing a constant specific growth rate), different cultures initiated differently may reach different steady states. That is to say, when the concentrations of cells, nutrients and metabolites eventually stabilize in these continuous cultures, cultures that have been initiated in different ways may be characterized by significantly different metabolite profiles under substantially identical continuous culture conditions. This is referred to as multiple steady states. Each representative culture at a particular steady state characterized by its individual metabolite profile contains cells in that particular metabolic state. These different metabolic states reflect different pathways for carbon metabolism used by cells in the different metabolic states. A culture of cells that has been metabolically shifted so as to produce low levels of lactate will more efficiently convert carbon to biomass than a conventional cell culture. From an industrial perspective, directing the cells to a metabolic state in which the nutrients are preferentially converted to biomass and potentially, various useful products (e.g., IgG), rather than extraneous metabolites, such as lactate, is highly desirable.

Alteration of metabolism in a number of anchorage-dependent cell lines, which must attach to a surface in order to survive and grow, was previously demonstrated using confluent cells (thus a relatively constant cell concentration in culture) attached on microcarriers. (Hu, W.-S. et al., in: *Large Scale Mammalian Cell Culture Technology.* Ed. A. S. Lubineicky, pp. 451–481, Marcel Dekker, Inc., New York, N.Y., (1990)). These microcarriers were small beads of about 200 µm in diameter which allowed cells to grow on them and be suspended in a spinner flask or a fermentor for cultivation. These cells, once grown to confluence, stopped growing (called contact inhibition) or grew substantially slower. Therefore, they could be grown at almost constant cell concentration. When cell concentration is constant, it is relatively easy to keep the nutrients in the cell culture at a constant rate. It was reported that a low glucose concentration gave rise to a metabolic state with a low lactate production.

However, numerous difficulties have been encountered in altering the metabolism of cells in suspension. Most suspension cells (except a few which cannot be cultivated easily in culture, such as some blood cells) cannot be "growth arrested" (i.e., not growing and not dying) in culture. Because their cell concentration changes in culture, their nutritional demand also changes with time. If one wants to keep the nutrient level in the culture constant, the nutrient supply rate must also change with demand. Continuous and dynamic feeding of nutrients is therefore needed to control the concentration at set point level. This usually requires an estimation of the metabolic demand of the cells relying on some on-line measurements. The estimated demand is then used to calculate the amount of nutrient needed to be fed in order to keep their concentrations at the set point. Such measurements, estimation, and feeding need to be performed at rather frequent intervals, otherwise, cell starvation or even cell death may occur. It is extremely difficult to perform these measurements manually over a long cultivation period, which sometimes lasts weeks. This is especially critical for hybridoma cells, as even a short duration of starvation may lead to apoptosis (or programmed cell death).

Glucose concentration can be measured on-line; when glucose concentration decreases to below the set point, glucose solution can be fed to the continuous culture to bring the glucose concentration back to the set point. Additionally, since cells consume not only glucose but also other nutrients, it is often preferably to feed a solution containing glucose and other nutrients. Determining how much of the other nutrients need to be supplied, and how and when these amounts need to adjusted, can be done by performing on-line measurements of these nutrients, but this is very difficult and expensive. Because cells usually consume glucose and other nutrients at certain ratios (often referred to as a stoichiometric ratio), a convenient alternative is to feed other nutrients at stoichiometric ratios to glucose while actually monitoring only glucose levels. This is a good alternative where there has been no metabolic shift, since in conventional continuous cultures such stoichiometric ratios usually are relatively constant, and dynamic feeding can be performed using stoichiometric ratios established by prior experience. Complications arise, however, if the metabolic shift occurs and the cell metabolism, along with stoichiometric ratios, gradually changes during cultivation.

For example, in a fed-batch culture of hybridoma cells that secrete IgG monoclonal antibody, W. Zhou et al. (*Biotechnol. Bioeng.*, 46, 579–587 (1995)) were able to achieve a high viable cell concentration using on-line nutrient feeding designed to maintain the glucose concentration at a low level throughout the exponential growth period. Lactate production was reduced to near zero toward the end of cultivation. At the beginning of the cultivation 85% of the glucose carbons were excreted as lactate; each mole of glucose consumed was accompanied by about one mole of oxygen consumption. Toward the end of the cultivation, almost no glucose carbon was excreted as lactate and the molar stoichiometric ratio between oxygen and glucose increased to six, evidencing a metabolic shift in the metabolism of glucose. With the resultant lower degree of accumulation of both lactate and ammonia, a high cell concentration of $10^7$ cells/ml and a high viability (>95%) was achieved. The final product concentration (IgG) for the metabolically-shifted fed-batch culture was 65 mg/mL. In contrast, the IgG titer for this particular clone in a comparable batch culture in a high lactate production state in the defined medium was only 8 mg/mL.

In the absence of the metabolic shift that characterizes the present invention, the accumulation of lactate, and possibly also ammonia, causes the viability in a fed-batch culture to decrease quickly. In reported fed-batch cultures (Bibila et al, *Biotechnol. Prog.*, 10, 87–96 (1994); Zie and Wang, *Biotechnol. Bioeng.*, 17, 1175–1189 (1994)) which did not first elicit metabolic shift, none could achieve an over 90% viability when the cell concentration reached the maximum. Zhou et al. restricted both glucose and glutamine concentration to low concentrations of 0.5 mM and 0.2 mM respectively, during the growth state of a fed-batch culture (Zhou et al., *Cytotechnology*, 24, 99–108 (1997)). The initial concentration of glutamine in a typical batch culture ranges from 1 mM to 6 mM. During cell growth, the glutamine concentration decreases gradually to various levels. For most cells, the complete depletion of glutamine causes the cessation of cell growth or even cell death. A metabolic shift with reduced lactate production was observed, and significant reduction of ammonia production was also seen. However, even with the metabolic shift, the viable cell concentration decreased after reaching a peak and the culture had to be terminated due to low viability. It is an object of this invention to sustain the culture in a state of high cell concentration, high viability and at a metabolically shifted state.

The present invention thus involves initiating a continuous cell culture from a fed-batch cell culture containing cells that have been metabolically shifted to redirect carbons from lactate production to biomass accumulation. This "metabolic shift" can be initiated, aided and/or maintained by, among other things, restricting the amount of glucose delivered to the cells, as further described below. Thus, the metabolic shift in the fed-batch culture is preferably achieved by restricting the glucose concentration in a first nutrient feed. The fed-batch culture is preferably maintained for at least about 50 hours, preferably about 50 hours to about 100 hours, up to about 200 hours. The metabolically shifted fed-batch cell culture is then converted to a continuous cell culture, which is maintained in the metabolically shifted state, preferably by manipulating the glucose concentration in a second nutrient feed.

The method of the invention is well-suited to use in a bioreactor, particularly a chemostat, and finds application in both industrial scale and smaller scale operations. Furthermore, because the accumulation of undesired metabolites in the continuous culture of the present invention is minimized, nutrient concentration in the feed medium can, during the course of the continuous culture, be further increased to increase cell concentration. In the absence of a metabolic shift, any further increase in glucose, glutamine or amino acid concentration will either not increase cell concentration, or only have a limited effect because the cell concentration is limited by the concentration of undesired metabolites. If, however, the cells have been metabolically shifted as described herein, increases cell density are no longer limited by the accumulation of undesired metabolites, and the nutrient concentration in the feed can be further increased from that in the typical continuous culture feed medium to yield increased cell concentration. Thus, the present invention optionally includes a step of increasing the concentrations of one or more nutrients such as glucose, glutamine, amino acids and other cellular components (such as lipid, phosphate) in the second nutrient feed during the course of the continuous culture to cause increased levels of nutrients in the continuous culture environment and thereby to further increase the cell concentration.

The first nutrient solution delivered to the fed-batch culture in step (a) is preferably a concentrated nutrient solution comprising glucose, and, optionally, glutamine, amino acids, and salt. In a preferred embodiment of the method, the concentrated nutrient feed of step (a) comprises glucose (preferably about 22 to 67 mM), and, optionally, glutamine (preferably about 1 to about 40 mM), and at least one amino acid (preferably about 2–10 fold higher amino acid concentration as that in the medium). The first nutrient solution optionally contains bulk salts (in a concentration ranging from near zero up to about the same concentration as that in the medium). In a fed-batch culture the culture fluid is not being withdrawn from the bioreactors; therefore, it is common practice for the nutrient solution fed into the bioreactor to be in a very concentrated form to avoid adding too much liquid to the bioreactor, which would cause a large increase in the culture volume. The cell concentration in the fed-batch culture can be increased to about $3\times10^6$ cells/mL, preferably up to about $1.0\times10^7$ cells/mL or higher, for example, preferably with a viability of greater than about 90%. Cell concentration measurements (e.g., turbidity measurements, microscopic counting with a hemocytometer, etc.) can be performed either off-line by counting cells or on-line by optical methods.

Step (a) optionally includes periodically (i) measuring the oxygen glucose concentration in the fed-batch cell culture; (ii) measuring the oxygen consumption of the fed-batch culture; (iii) calculating the stoichiometric ratio of glucose in the fed-batch cell culture to oxygen consumption; and (iv) adjusting the feeding rate of the nutrient solution according to the new value of the glucose consumption to oxygen consumption stoichiometric ratio so as to maintain the glucose concentration in the fed-batch cell culture of about 0.05 mM to about 0.4 mM.

Glucose concentration in the culture can be measured, for example, by an enzymatic method. Oxygen consumption can be determined using on-line measurement of oxygen uptake rate as described in Zhou et al., *Biotechnol. Bioeng.*, 46, 579–587 (1995). In general, useful and suitable methods for metabolite concentration measurement and analysis are set forth in Zhou et al., *Biotechnol. Bioeng.*, 46, 579–587 (1995), and Zhou et al., *Biotechnol. Bioeng.*, 44, 170–177 (1994), both of which are incorporated herein in their entirety. The consumption rate is calculated by taking the difference in metabolite or nutrient concentrations of two consecutive samples and divided by the time interval. The calculation of the specific nutrient consumption rate or production rate (such as specific glucose consumption rate or specific lactate production rate) is well-documented in standard biochemical engineering textbooks (Wang, et al., *Fermentation and Enzyme Technology*. p. 79, John Wiley and Sons, (1979) incorporated herein by reference in its entirety). The molar stoichiometric ratio of lactate produced to glucose consumed can be calculated by taking the ratio of the specific rate of lactic acid production ($q_{lactate}$) to the specific rate of glucose consumption ($q_{glucose}$), or by dividing the amount of lactic acid produced in consecutive sampling time points over the amount of glucose consumed during the same time period.

The second nutrient solution delivered to the continuous cell culture in step (c) comprises at least one component of the growth medium. In a preferred embodiment of the method, the second nutrient solution comprises glucose, glutamine and other amino acids at levels equal to or higher than the batch growth medium. The initial glucose concentration in the second nutrient solution is preferably about 5 mM to about 67 mM, more preferably about 5 mM to about 25 mM. Preferably, the glucose concentration in the second nutrient solution is at least about 5 mM. The concentration of glutamine in the second nutrient solution is preferably about 1 mM to about 40 mM. Amino acids are preferably one- to four-fold concentrated from that in the continuous culture medium. The concentration of the nutrients in the second nutrient solution delivered to the continuous cell cultures may be lower than that of the first nutrient solution for the fed-batch culture. This is because that during the continuous culture fluid is continuously being withdrawn, therefore the culture volume can be maintained at a constant level. In a fed-batch culture a concentrated nutrient feed is typically used to avoid drastically increasing the culture volume.

The continuous cell culture can be maintained for a substantial period of time, preferably about 300 hours, more preferably about 1000 hours, most preferably about 1300 hours, while preferably maintaining in the continuous cell culture a glucose concentration of about 0.05 mM to about 0.4 mM and a lactate concentration of less than about 40 mM. More preferably, the lactate concentration in the continuous culture environment is less than about 30 mM, even more preferably less than about 5 mM. In a particularly preferred embodiment, the lactate concentration is less than about 2 mM, preferably less than about 1 mM. The lactate concentration during the continuous culture preferably remains under the preferred concentrations, but it should nonetheless be understood in the spirit of the invention that temporary increases in lactate concentration above the stated levels can optionally be accommodated as long as the average lactate concentration during the course of the continuous culture remains below the stated levels. During the period of continuous culture, a cell density of at least about $4\times10^6$ viable cells/mL is preferably maintained.

Optionally, the method can include, at one or more points during the continuous culture, one or more of the following actions:

(i) increasing the amino acids in the third nutrient solution to up to five-fold of the concentration in the medium;

(ii) increasing the dilution rate (defined as the ratio of the feed rate, which is typically stated in liters per hour (L/hr), to the reactor volume (in liters, L)); and (iii) increasing the glucose concentration in the second nutrient solution.

These actions are intended to further increase cell density while maintaining the cells in the metabolically shifted state.

The "metabolic shift" that characterizes the cells cultured according to the present invention is evidenced by the sustained low level of lactate production of the cells. Conveniently, this change in carbon metabolism is accompanied by a characteristic change in the molar stoichiometric ratio of lactate produced to glucose consumed for the cell culture. As used herein the stoichiometric ratio is an "instantaneous" ratio, meaning the ratio of the lactate produced to that of glucose consumed in consecutive measurements from samples of at most hours apart. Such a ratio differs from those calculated from the cumulative data, meaning measurements from samples which span over days, for example, the stoichiometric ratio may also be calculated from the beginning of the culture. In that case, it is calculated by the total glucose consumed since the initiation of the culture and the total amount of lactic acid produced during that same time period. That stoichiometric ratio may differ from the instantaneously calculated ratio used to characterize the metabolic shift of present invention.

A typical lactate to glucose molar stoichiometric ratio for conventional, non-metabolically shifted cell cultures is about 2. The metabolically-shifted fed-batch culture produced in step (a) of the present method, and the continuous cultures after conversion from the fed-batch culture, are each preferably characterized by a lactate to glucose molar stoichiometric ratio of less than about 1, more preferably less than about 0.8, even more preferably less than about 0.5. A lactate to glucose molar stoichiometric ratio of about 0.2 to about 0.4 in the continuous culture is advantageous according to the method of the invention. In the most preferably embodiment, this lactate to glucose molar stoichiometric ratio is less than about 0.1.

The lactate concentration in the fed-batch culture produced in step (a), and/or of the continuous culture during step (c), is preferably less than about 30 mM, more preferably less than about 10 mM, even more preferably less than 5 mM. In the most preferred embodiments, lactate concentration in the continuous culture environment averages less than 2 mM, more preferably less than 1 mM, during the period of continuous culture. Lactate concentration can be measured, for example, by determining the amount of base needed to neutralize pH. Preferably, the lactate concentration is measured enzymatically.

Optionally, the method of the invention includes a step of restricting the amount of glutamine delivered to the cells during the continuous culture. In conventional non-metabolically-shifted cell cultures, the glutamine concentration in the cell medium is typically about 0.5 to about 6 mM. In the method of the present invention, the amount of glutamine in the second nutrient feed is optionally reduced after the metabolically-shifted cells have been converted to a continuous culture, such that the glutamine concentration in the continuous cell culture environment is about 0.01 mM to about 0.1 mM. When the metabolic shift of the present invention is followed by a reduction in glutamine levels, both lactate and ammonia production are reduced. Reduction of ammonia ($NH_4^+$) production is desirable because a high concentration of ammonia (for most cell lines, a concentration higher than 6.0 mM) is growth inhibitory. Preferably, the molar stoichiometric ratio of ammonia produced to glutamine consumed in the continuous culture is less than about 1.3, more preferably between about 0.5 and about 1.3.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

EXAMPLE 1

High Density Continuous Culture of Hybridoma Cells Maintaining Altered Carbon Metabolism Hybridoma cell line and culture media. The study entailed in this example used a mouse-mouse hybridoma cell line (MAK, as described in Zhou and Hu, *Biotechnol. Bioeng.*, 47, 181–185 (1995)) which produces IgG monoclonal antibody. Cells were maintained in a 1:1 mixture of Dulbecco's modified Eagle's medium (DMEM) (GIBCO) and Hma's F12 medium (GIBCO) supplemented with transferrin, 2-mercaptoethanol, ethanolamine, L-ascorbic acid, sodium selenite, putrescine and Pluronic F68 (SIGMA, FLUKA). The concentrations of glucose (SIGMA) and glutamine (SIGMA) in this medium were 17.4 mM (3.15 g/L) and 4 mM respectively. For the fed-batch experiments, the starting medium used was the same as the maintenance medium except that the glucose and glutamine concentrations, which were reduced to 0.72 mM (0.13 g/L) and 0.17 mM respectively. The feed for the fed-batch culture was a ten-fold concentrated solution of the maintenance medium except that (i) the concentrations of the bulk salts (NaCl, KCl and $CaCl_2$) were not increased and (ii) the glucose concentration in the concentrated feed medium was 66.7 mM and the glutamine concentration in the concentrated feed medium was 40 mM.

Bioreactor set-up. The experiment was performed in an environmentally controlled room maintained at 37° C. using a 750-mL glass bioreactor with a working volume of 500 mL. The experimental set-up had been described by Zhou et al., *Biotechnol. Bioeng.*, 46, 579–587 (1995). The bioreactor was monitored and controlled using an IBM PC-XT equipped with a DT-2805 Data Acquisition Board (Data Translation Inc., Marlborough, Mass.) and two RS-232 boards. The culture pH, dissolved oxygen (DO) concentration, the mass of the feed medium, and the turbidity were acquired and recorded automatically. The culture pH was kept between 6.9 and 7.0. Air, oxygen and nitrogen gases were used to maintain the DO at 40% of air saturation. 5% $CO_2$ was maintained in the gas space. Aeration was achieved through the headspace and silicon tubing.

Oxygen uptake rate (OUR) was measured dynamically every hour using a procedure described by Zhou et al., *Biotechnol. Bioeng.*, 46, 579–587 (1995). To measure OUR, the DO was increased to 65% of air saturation and was subsequently flushed with nitrogen to decrease the oxygen level in the medium down to 30%. The time profile of DO between 50% and 30% was used to calculate OUR. The volumetric oxygen mass transfer coefficient ($K_L a$) was determined prior to inoculation using the same method. The $K_L a$ value remained constant throughout the cultivation.

To convert the measured oxygen partial pressure into oxygen concentration, Henry's coefficient for the culture medium was assumed to be the same as that for pure water (952.27 atmosphere-L/mole) at 37° C. Cumulative oxygen consumption was calculated by numerical integration of OUR through time.

Measurements. Off-line measurements are taken every 12 hours during every phase of the culture for analysis. Fresh samples were used to determine cell, glucose and lactate concentrations. The cell concentration was determined by microscopic counting with a hemocytometer. The viability was determined by the trypan blue dye exclusion method. The lactate concentration was measured enzymatically using a YSI Model 27 analyzer (Yellow Springs Instruments, Yellow Springs, Ohio). The glucose and ammonia concentrations were determined using enzyme-based assay kits (Sigma Chemical Co., St. Louis, Mo.). The osmolality was measured using a vapor pressure osmometer (Wescor Inc., Logan, Utah). The antibody titer was assayed by HPLC using a protein G affinity chromatography column (PerSeptive Biosystms, Cambridge, Mass.). The concentrations of the amino acids were measured by HPLC (Beckman) using reversed-phase chromatography and pre-column derivatization with orthophthaldialdehyde (OPA).

Figure 2:
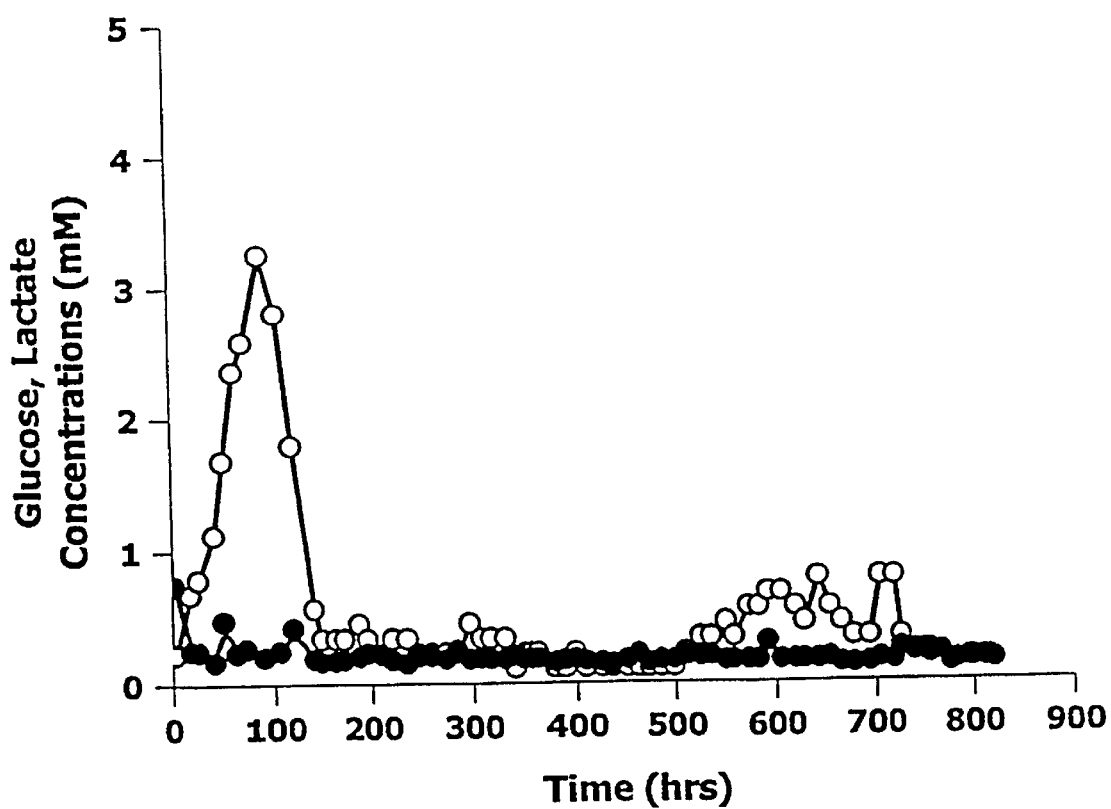
FIG. 2. Glucose (filled circles) and lactate (open circles) concentrations versus time in high density continuous culture of hybridoma cells according to the invention.

Low-lactate fed-batch cell culture converted to low-lactate continuous cell culture. The culture was initiated by innoculating exponentially growing hybridoma cells from a seed culture into the reactor at a concentration of $1.5 \times 10^5$ viable cells/mL. See, Zhou et al., *Biotechnol. Bioeng.*, 46, 579–587 (1995). The culture can be divided into six phases (FIG. 1). First was a short batch growth phase that lasted about seven hours to reduce the initial glucose concentration in the culture from 0.72 mM (0.13 g/L) to 0.28 mM (0.05 g/L) (FIG. 2) which is the desired setpoint for glucose control. The initial glucose concentration of 0.72 mM was higher than set-point to allow for time to conduct any hardware adjustment if necessary before the fed-batch phase. The initial glutamine concentration was 0.17 mM. This value decreased eventually to about 0.03 mM. OUR was measured and the cumulative oxygen consumption was calculated on-line. From past experiments an averaged stoichiometric ratio of glucose consumption to oxygen consumption was obtained. Using the on-line measurement of oxygen uptake, the amount of glucose consumed was estimated on-line. The culture was operated in a batch mode until glucose concentration fell to 0.28 mM (0.05 g/L) as estimated by on-line calculation of glucose concentration based on the measured oxygen consumption. At that time point (about 7 hours after initiation of the culture) feeding of the concentrated nutrient solution was initiated, representing the second phase of the culture.

From 7 hours to 105 hours (the second phase), the culture mode was fed-batch. The feed, as described above in the paragraph, "Hybridoma cell line and culture media," was added dynamically to replenish the consumed nutrients as estimated from the measured oxygen consumption rate during this phase of the culture. Feeding was every hour. The cell concentration rose from $0.15 \times 10^6$ viable cells/mL to $4.4 \times 10^6$/mL during that time, and the viability remained high at about 92%. The average growth rate at this point was about 0.034 hr$^{-1}$. During this fed-batch phase, samples were withdrawn periodically and the glucose concentration was measured off-line. The stoichiometric ratio of glucose consumption to oxygen consumption was calculated, and the stoichiometric coefficient used in the nutrient feeding was adjusted as needed to ensure that the glucose level remain close to set point, in this case, 0.28 mM. This ratio changed little after the first few samples, though, and was maintained for the duration of the fed-batch phase. At that time point the lactate concentration in the culture was 2.8 mM and the stoichiometric ratio of lactate produced to glucose consumed was lower than 0.1 mol/mol.

Phase three, representing continuous feeding, started at 105 hours with a dilution rate of 0.033 hr$^{-1}$. The feed contained 5 mM (0.9 g/L) of glucose and 2.8 mM glutamine, with all the other components, except bulk salts, at a concentration 1.6 times that of the basal medium DMEM/F12, with the corresponding increase in concentration of the media additives. At this point, the lactate concentration was 2.75 mM (0.245 g/L) and glucose was 0.24 mM (0.044 g/L). After continuous flow started, the viable cell concentration decreased to $4.1 \times 10^6$/mL, then increased to $5.0 \times 10^6$/mL. This concentration was maintained for 80 hours. The glucose concentration in the cell culture was always between 0.17 to 0.25 mM (0.03 to 0.05 g/L) during this time while lactate concentration decreased to 0.22 mM (0.02 g/L). The viability also decreased from about 92% at the start of continuous feeding to about 80%. The lactate to glucose ratio was on average 0.05 mol/mol, or only 0.025 g of lactate was produced for every gram of glucose consumed.

At 300 hours, representing the start of the fourth phase, all the amino acids in the continuous feed media except glutamine were fortified from 1.6× to 2.2× and feeding continued at the same dilution rate. When steady state was reached at about 400 hours, the viable cell concentration was $5.2 \times 10^6$/mL with an average viability of 70%. The glucose concentration in the cell culture was still maintained between 0.17 and 0.28 mM (0.03 g/L to 0.5 g/L) but the lactate concentration was on average about 0.11 mM (0.01 g/L). The average conversion of lactate from glucose decreased to 0.03 mol/mol as compared to the first steady state.

The dilution rate was changed from 0.033 hr$^{-1}$ to 0.036 hr$^{-1}$ at 490 hours, initiating the fifth phase of the culture. The cell concentration decreased to $4.0 \times 10^6$/mL which was maintained for at least 100 hours. Although the glucose concentration inside the reactor was maintained, the lactate concentration began to increase steadily from the initial value of 0.11 mM to 0.67 mM (0.01 g/L to 0.06 g/L) at about 610 hours. The viable cell concentration started increasing again and reached $5.2 \times 10^6$/mL. The viability also increased to 90%.

At 710 hours, the sixth phase was initiated by increasing the glucose concentration in the continuous feed from about 5 mM (0.9 g/L) to about 6.4 mM (1.15 g/L). The corresponding increase in cell concentration was almost instantaneous. Within 20 hours, the cell concentration had reached $7.0 \times 10^6$/mL with a viability of 90%. The viability eventually settled to an average of 87% with the final viable cell density of $7.5 \times 10^6$/mL.

For this entire run, the lactate production to glucose consumption ratio was usually less than 0.1 mol/mol. This is very different from the observed ratio in literature which ranges from 1.2 to 2.0 mol/mol. This observation suggests that the cells have entered an alternate physiological state.

Conventional continuous cell culture (control culture). A metabolic state characterized by relatively low lactate production is not normally seen in batch or continuous culture. Continuous cultures initiated from a batch culture almost invariably reach a steady state with a high lactate production rate and a high lactate yield from glucose. To illustrate this, a continuous culture was initiated from a batch culture and switched directly to a continuous mode after 48 hours using a dilution rate and feed media as in the culture described above. Without first eliciting a metabolic shift through fed-batch culture, most of the glucose consumed will be converted to lactate, and the maximum cell concentration achieved will be lower.

Figure 3:
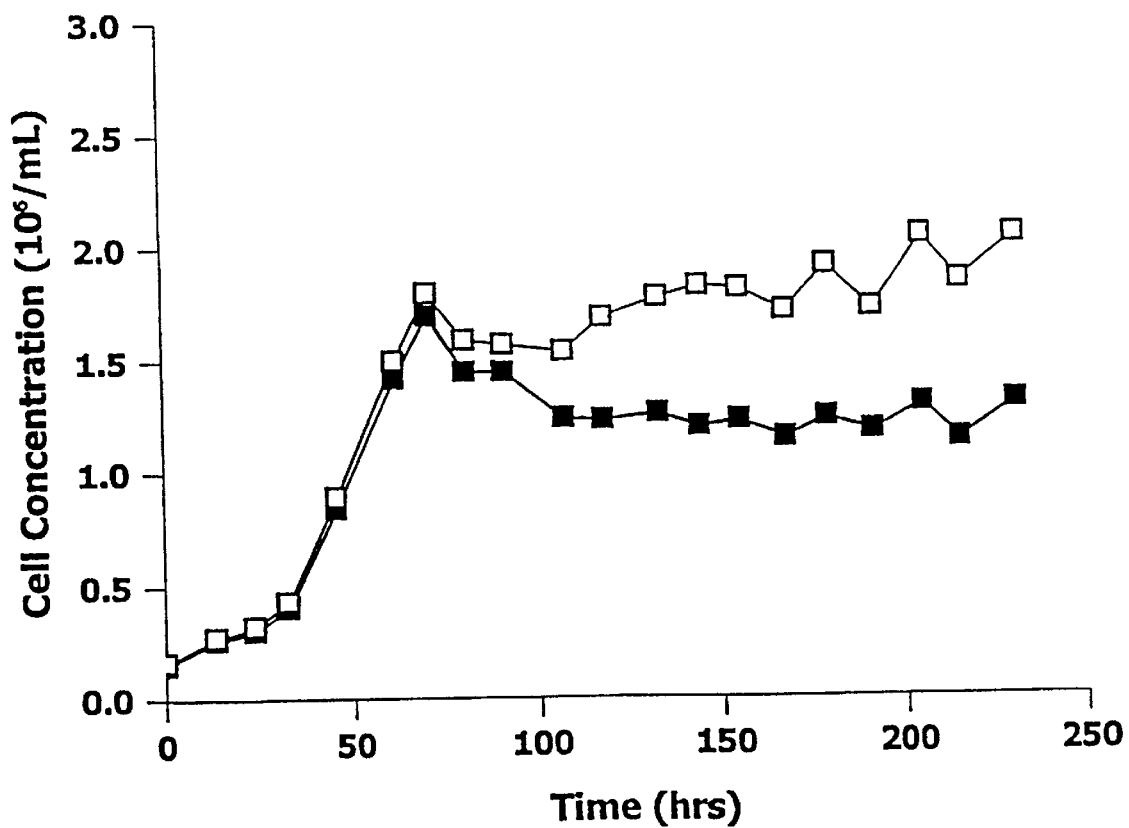
FIG. 3. Viable (filled squares) and total (open squares) cell concentrations versus time in conventional continuous culture of hybridoma cells.
Figure 4:
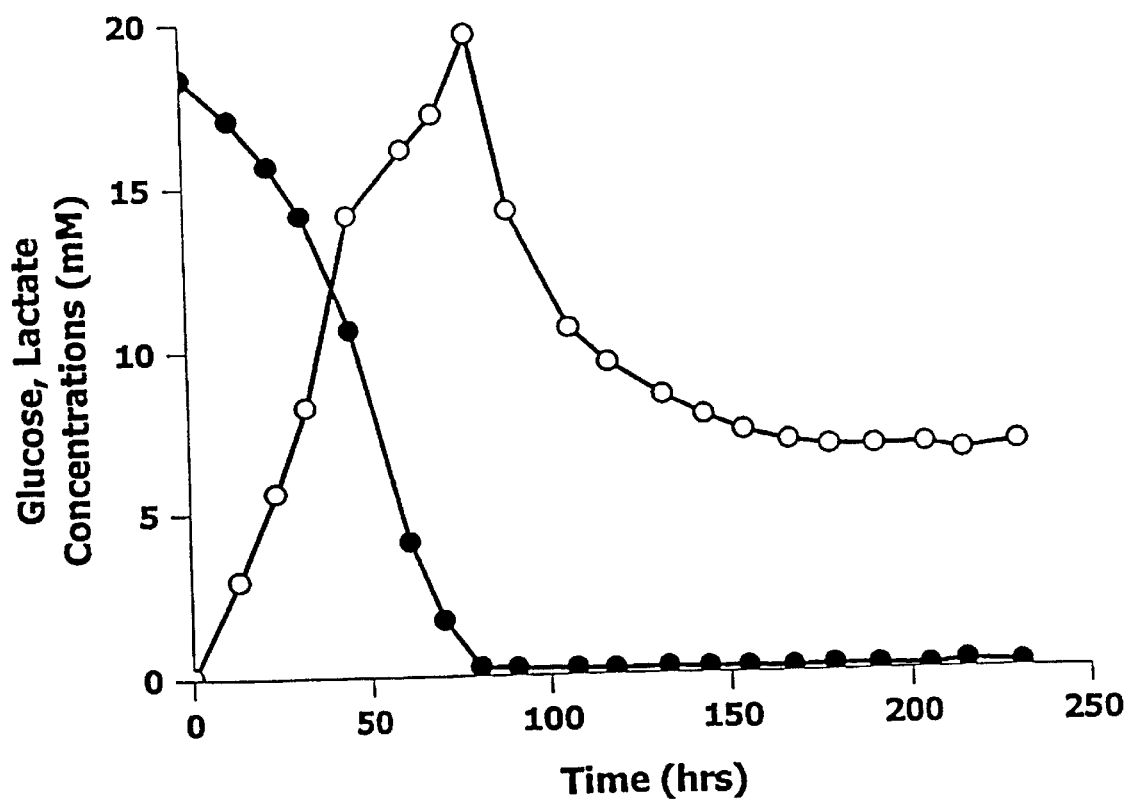
FIG. 4. Glucose (filled circles) and lactate (open circles) concentrations versus time in conventional continuous culture of hybridoma cells.

Cells were inoculated into a spinner flask with an initial viable cell concentration of $0.15 \times 10^6$/mL (FIG. 3). The starting culture medium was the same starting media used in fed-batch except that it had a higher initial glucose concentration (17.5 mM) and glutamine concentration (4 mM) (FIG. 4). The cells were allowed to grow in batch mode for 46 hours, until the viable cell concentration reached $0.84 \times 10^6$/mL. Continuous feeding using the same feed media used in the first culture and at a dilution rate of 0.031 hr$^{-1}$ was started then. The cells continued to increase to $1.7 \times 10^6$/mL with a viability >90%. After 70 hours, however, the viable cell concentration started to decrease steadily until it plateaued at $1.25 \times 10^6$/mL. The viability also decreased to a steady state value of 65%.

The glucose concentration in the reactor was maintained between 0.17 mM and 0.20 mM (0.03 g/L and 0.05 g/L), but the lactate continued to be produced at a high rate to give a lactate production to glucose consumption ratio of 1.3 mol/mol at steady state. The lactate concentration stabilized at 6.9 mM (0.615 g/L). The feed for this control culture contained only 5 mM of glucose (same as phase three of the metabolically shifted culture). Had a higher concentration of glucose been used, the cell concentration and lactate concentration would have been higher, but the lactate to glucose stoichiometric ratio would have remained about the same.

Figure 5:
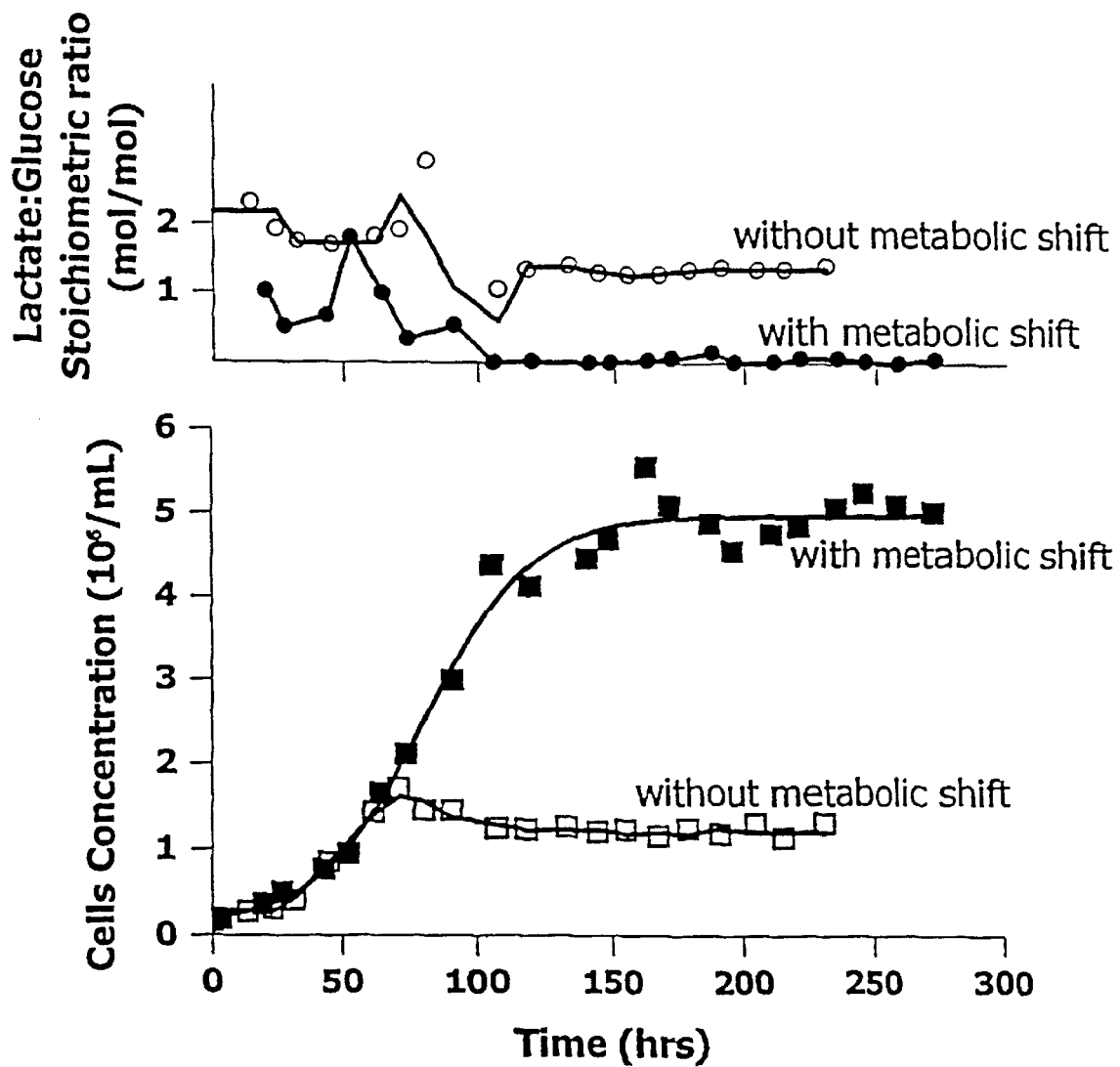
FIG. 5. Comparison of the lactate to glucose stoichiometric ratio and the cell concentrations for the two cultures in Example 1. The curves for the culture with metabolic shift only show the results during Phase Three of the continuous culture.
Figure 6:
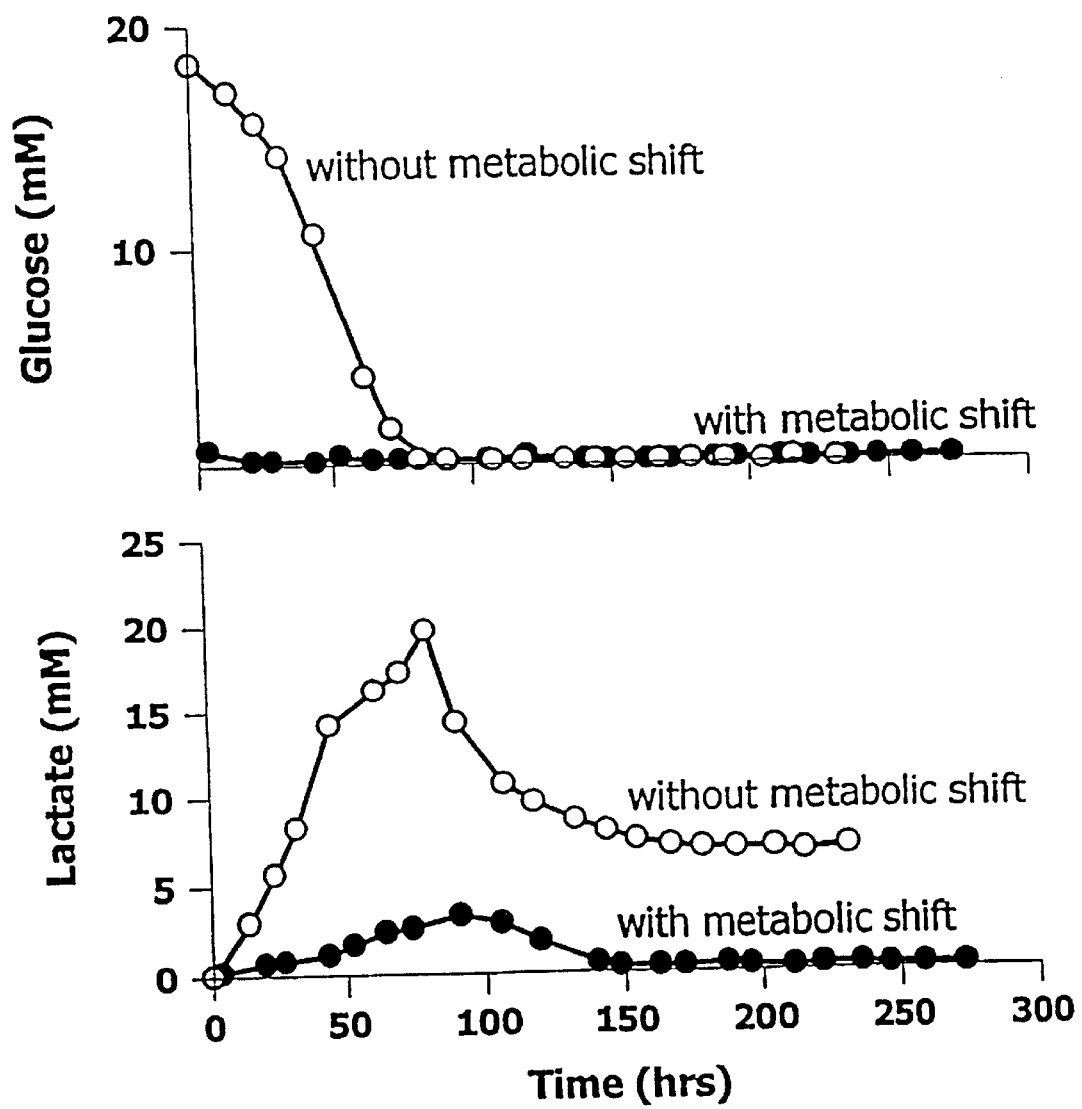
FIG. 6. Glucose and lactate concentrations for the two cultures of Example 1.
Figure 7:
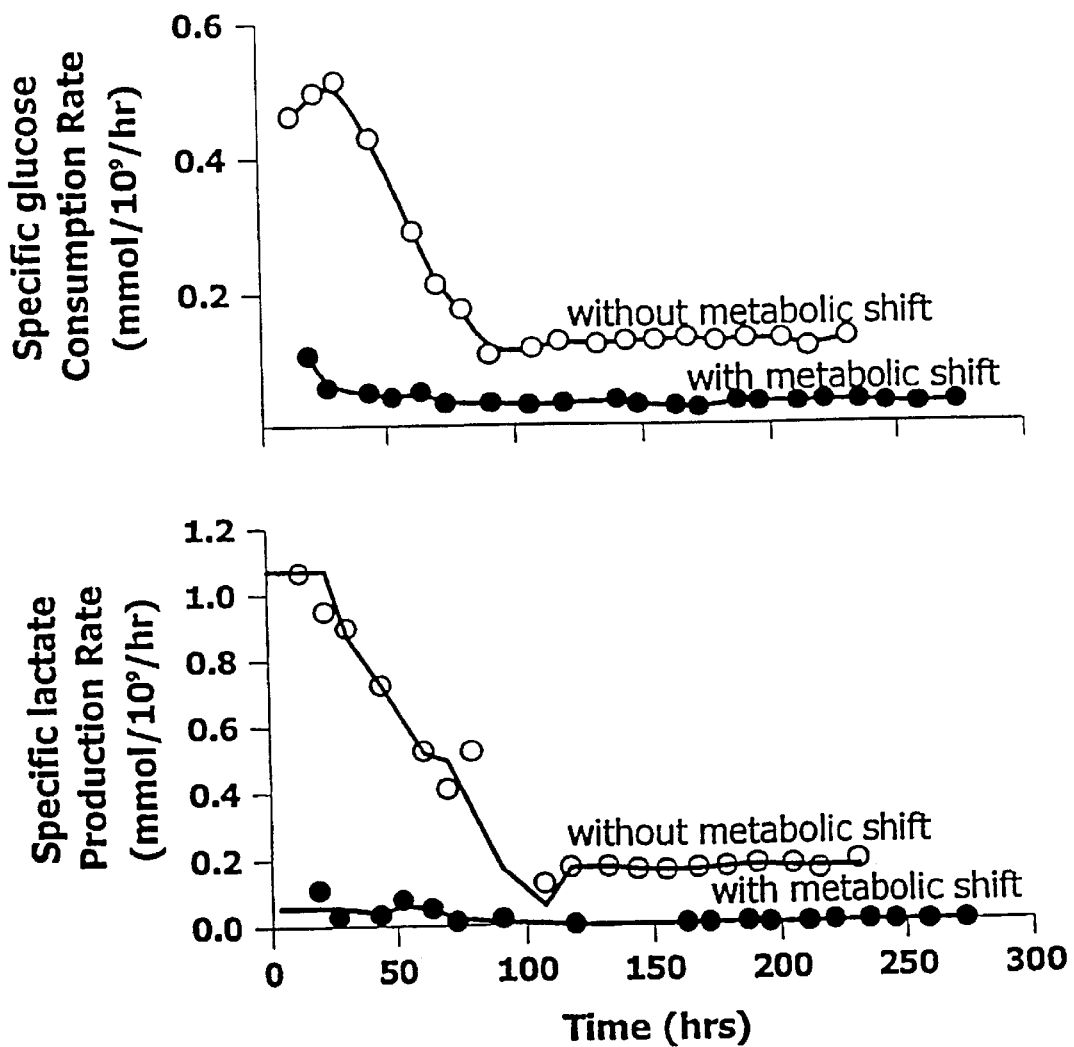
FIG. 7. Comparison of specific rates of glucose consumption and lactate production for the two cultures in Example 1.

Parameters for the control culture and the metabolically shifted culture are compared in FIGS. 5, 6 and 7. FIG. 5 compares cell densities and lactate to glucose molar stoichiometric ratios; FIG. 6 compares of glucose and lactate concentrations; FIG. 7 compares specific glucose consumption rates and specific lactate production rates; and the table in FIG. 8 compares a number of different rates and metabolic quotients. From these results, it is apparent that it is possible to cause a change in cell metabolism in a fed-batch culture from a conventional, glycolytic metabolic state to a low-lactate-producing ("efficient") metabolic state, and to maintain that change for a sustained period in continuous culture. The steady state cell density for this metabolically shifted culture is higher than for a typical glycolytic culture. These data provide convincing evidence that under identical operating conditions, animal cells in cultures that have been initiated in different ways can reach and maintain distinct metabolic states, giving rise to steady state multiplicity.

EXAMPLE 2

Continuous Culture of Hybridoma Cells with Intermediate Metabolism

This example followed similar steps as Example 1. The cell line and methods of culture, including maintenance, bioreactor setup, measurements, fed-batch culture operations, and feed preparation and dilution rate during the continuous culture phase, were all identical with Example 1.

Figure 9:
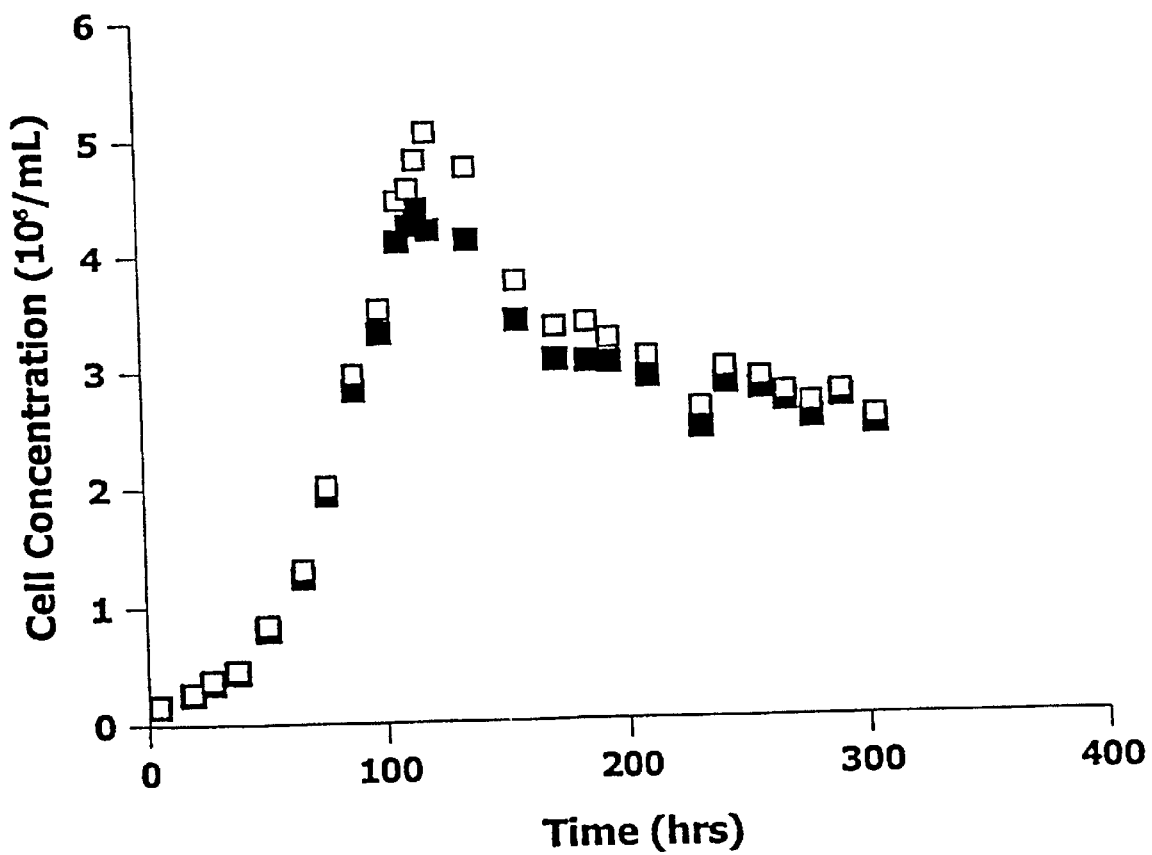
FIG. 9. Viable (filled squares) and total (open squares) cell concentrations versus time for continuous culture with cells in the intermediate metabolism (Example 2).

The culture was initiated by innoculating exponentially growing hybridoma cells from a seed culture into the reactor at a concentration of $1.5 \times 10^5$ viable cells/mL. The batch growth phase lasted 19 hours to reduce the initial glucose concentration in the culture from 0.59 mM (0.10 g/L) to 0.28 mM (0.05 g/L) as estimated by on-line calculation of glucose concentration based on the measured oxygen consumption (FIG. 9).

The initial glutamine concentration was 0.17 mM. It decreased eventually to about 0.03 mM by the end of the batch mode (Phase I). At that time point, feeding of the concentrated nutrient solution was initiated, representing the second phase of the culture.

From 19 hours to 121 hours, the culture mode was fed-batch (Phase II). The feed, as described above in the paragraph, "Hybridoma cell line and culture media," in example 1 was added dynamically to replenish the consumed nutrients as estimated from the measured oxygen consumption rate during this phase of the culture. The cell concentration rose from $0.15 \times 10^6$ viable cells/mL to $4.4 \times 10^6$/mL during that time, and the viability remained high at about 92%. During this fed-batch phase, samples were withdrawn periodically and the glucose concentration was measured off-line. The stoichiometric ratio of glucose consumption to oxygen consumption was calculated, and the stoichiometric coefficient used in the nutrient feeding was adjusted as needed to ensure that the glucose level remain close to set point, in this case, 0.28 mM. This stoichiometric ratio changed little after the first few samples, and was maintained for the duration of the fed-batch phase. At the end of phase II, the lactate concentration in the culture environment was 1.9 mM and the molar stoichiometric ratio of lactate produced to glucose consumed was less than 0.5.

Figure 10:
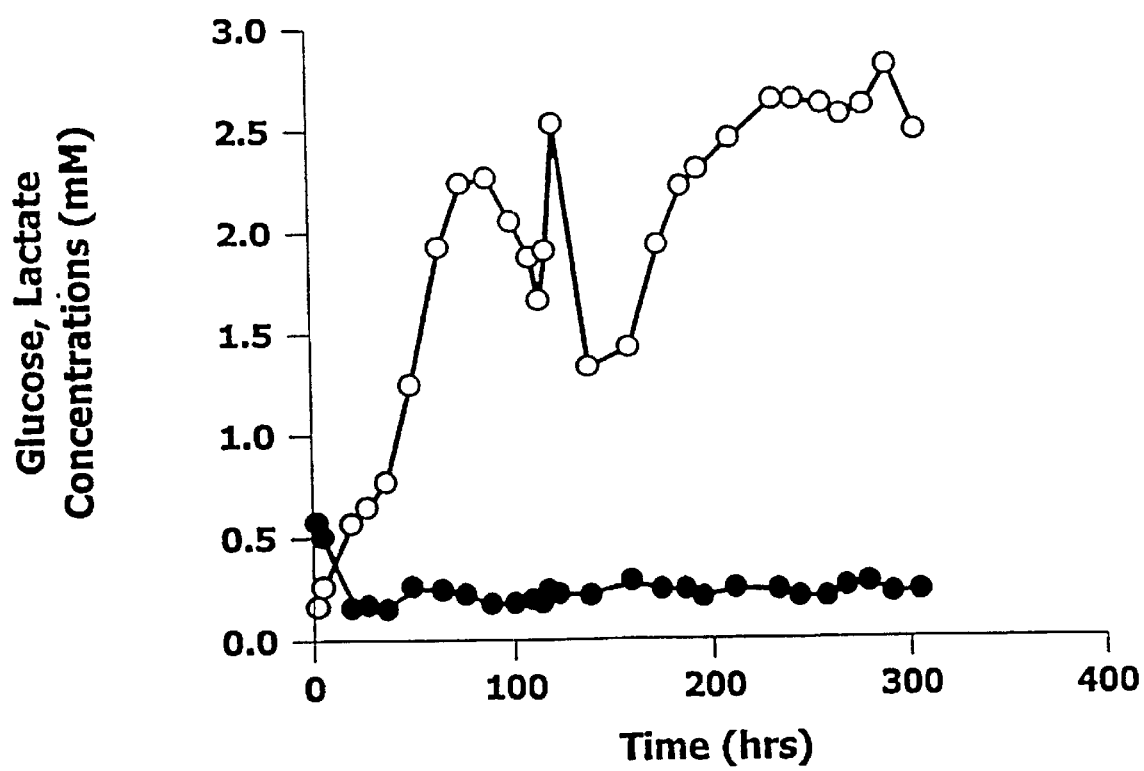
FIG. 10. Glucose (filled circles) and lactate (open circles) concentrations versus time for continuous culture with cells in the intermediate metabolism (Example 2).
Figure 11:
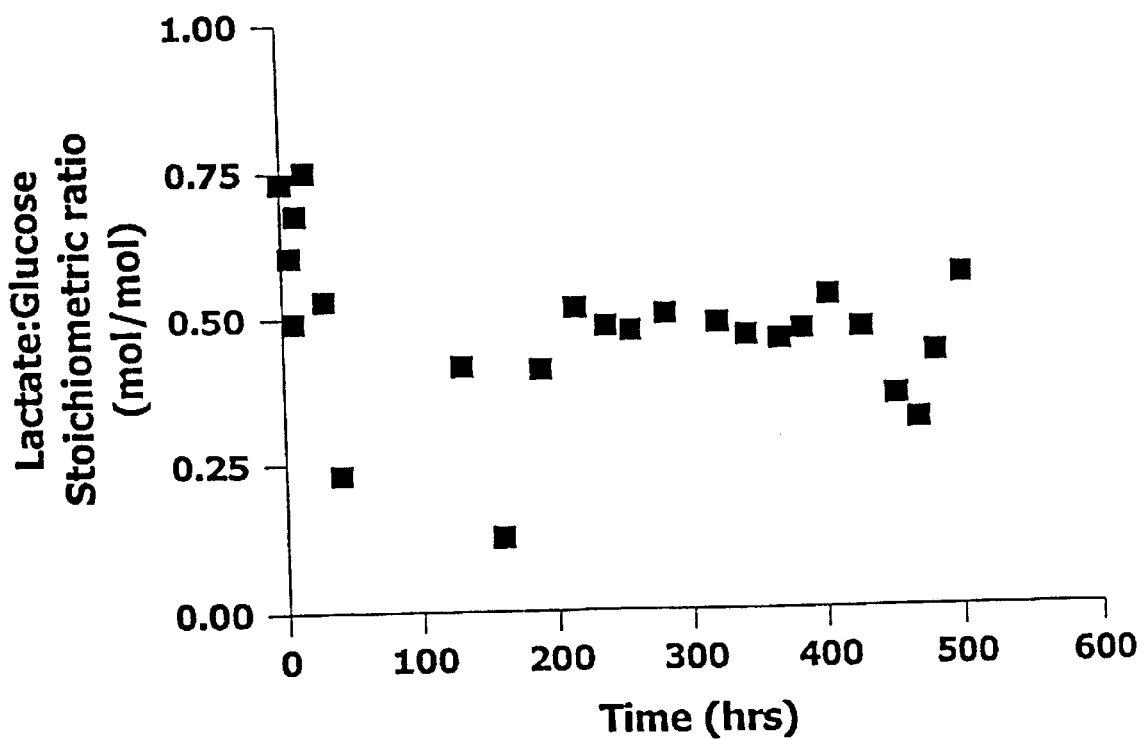
FIG. 11. Lactate to glucose stoichiometric ratio for continuous culture with cells in the intermediate metabolism (Example 2).

Phase III, representing continuous culture, started at 122 hours with a dilution rate of 0.034 $hr^{-1}$. The feed contained 5 mM (0.9 g/L) of glucose and 2.8 mM glutamine, with all the other components, except bulk salts, at a concentration 1.6 times that of the basal medium DMEM/F12, with the corresponding increase in concentration of the media additives. At this point, the lactate concentration was 2.53 mM (0.245 g/L) and glucose was 0.22 mM (0.04 g/L). After continuous flow started, the viable cell concentration decreased steadily until it reached a steady state valued of $2.7 \times 10^6$/mL. The steady state lactate concentration was 2.64 mM while the glucose concentration was 0.2 mM. The lactate to glucose molar stoichiometric ratio was 0.46 mol/mol. FIG. 10 shows the glucose and lactate concentration in the culture environment. FIG. 11 shows the molar stoichiometric ratio of lactate production to glucose consumption. In this example, the molar stoichiometric ratio of lactate production to glucose consumption was about 0.3 to 0.4, higher than the metabolically shifted culture in Example 1, but lower than the one without metabolic shift. As a result of the intermediate efficiency, the steady state cell concentration was also in between those two cultures.

EXAMPLE 3

High Cell Density Continuous Culture of Hybridoma Cells

This example followed similar steps as Example 1 and 2. The cell line and methods of culture, including maintenance, bioreactor setup, measurements, fed-batch culture operations, and feed preparation and dilution rate during the continuous culture phase, have already been described in Example 1.

The culture was initiated by innoculating exponentially growing hybridoma cells from a seed culture into the reactor at a concentration of $1.5 \times 10^5$ viable cells/mL. The batch growth phase lasted 10 hours to reduce the initial glucose concentration in the culture from 0.59 mM (0.10 g/L) to 0.28 mM (0.05 g/L) which is the desired setpoint for glucose control.

The glutamine concentration, which was 0.13 mM initially, decreased to about 0.06 mM during the batch phase of the culture. The culture was operated in a batch mode until glucose concentration fell to 0.28 mM (0.05 g/L) as estimated by on-line calculation of glucose concentration based on the measured oxygen consumption. At that point ($10^{th}$ hr) feeding of the concentrated nutrient solution was initiated, representing the second phase of the culture.

Figure 12:
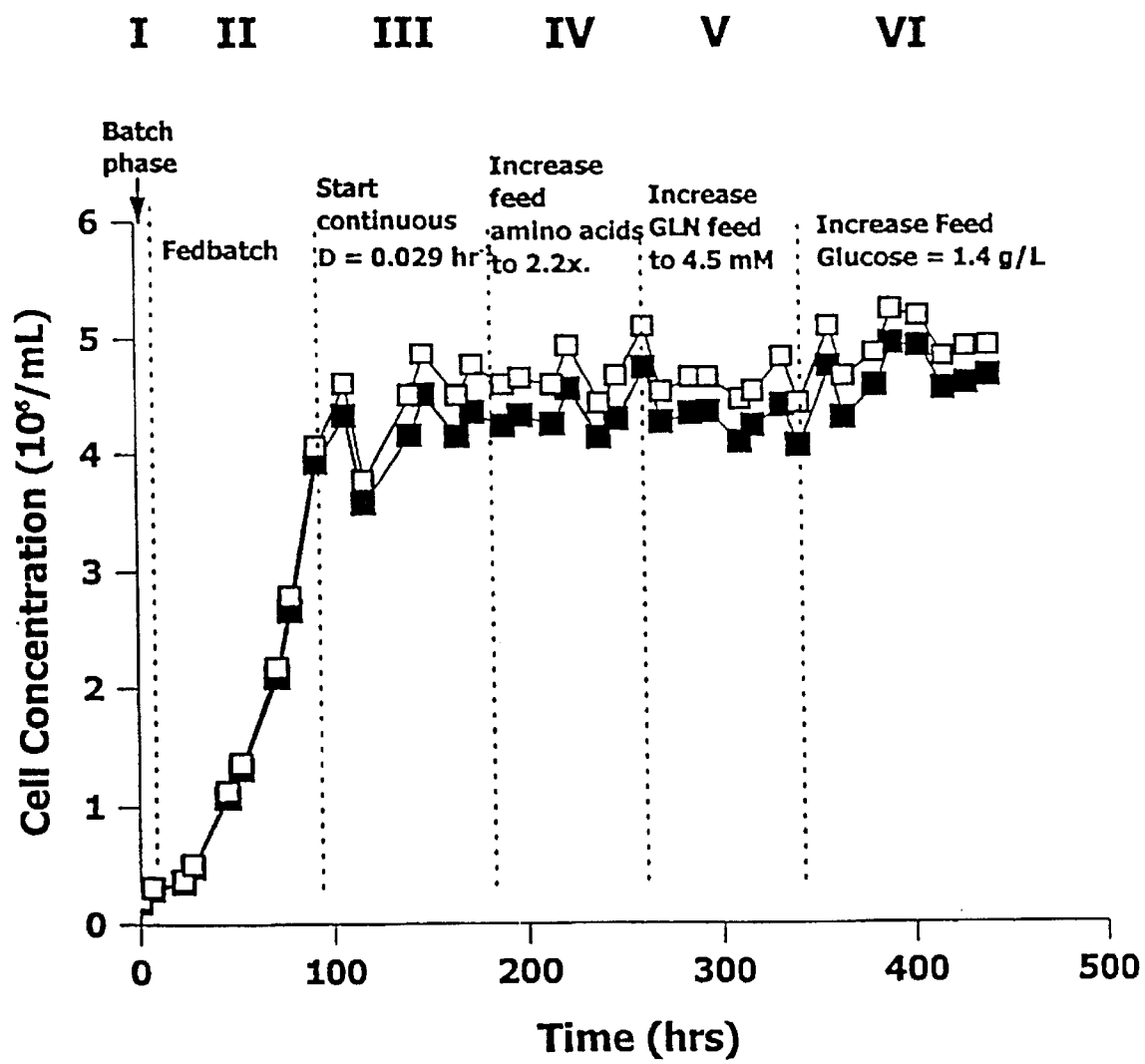
FIG. 12. Viable (filled squares) and total (open squares) cell concentrations versus time in high density continuous culture of hybridoma cells according to the invention (Example 3).
Figure 13:
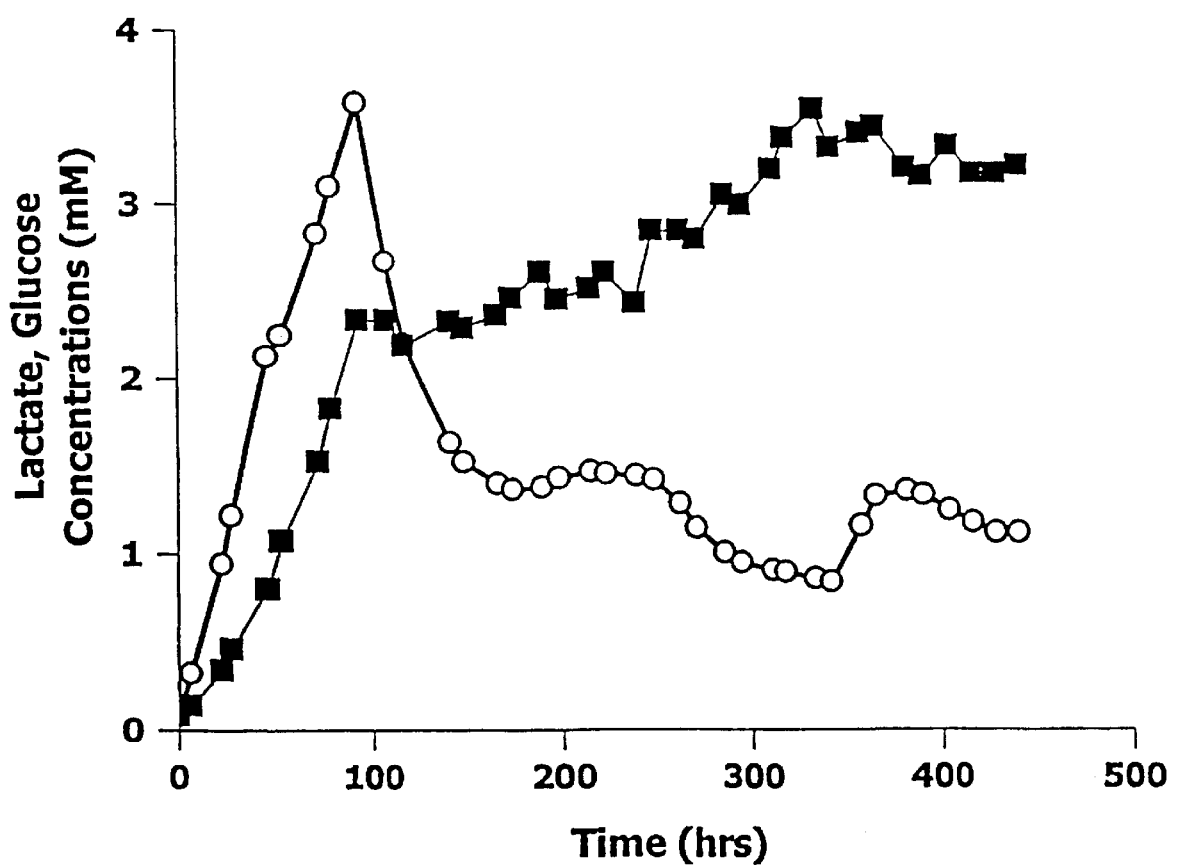
FIG. 13. Glucose (filled circles) and lactate (open circles) concentrations versus time high density continuous culture of hybridoma cells according to the invention (Example 3).
Figure 14:
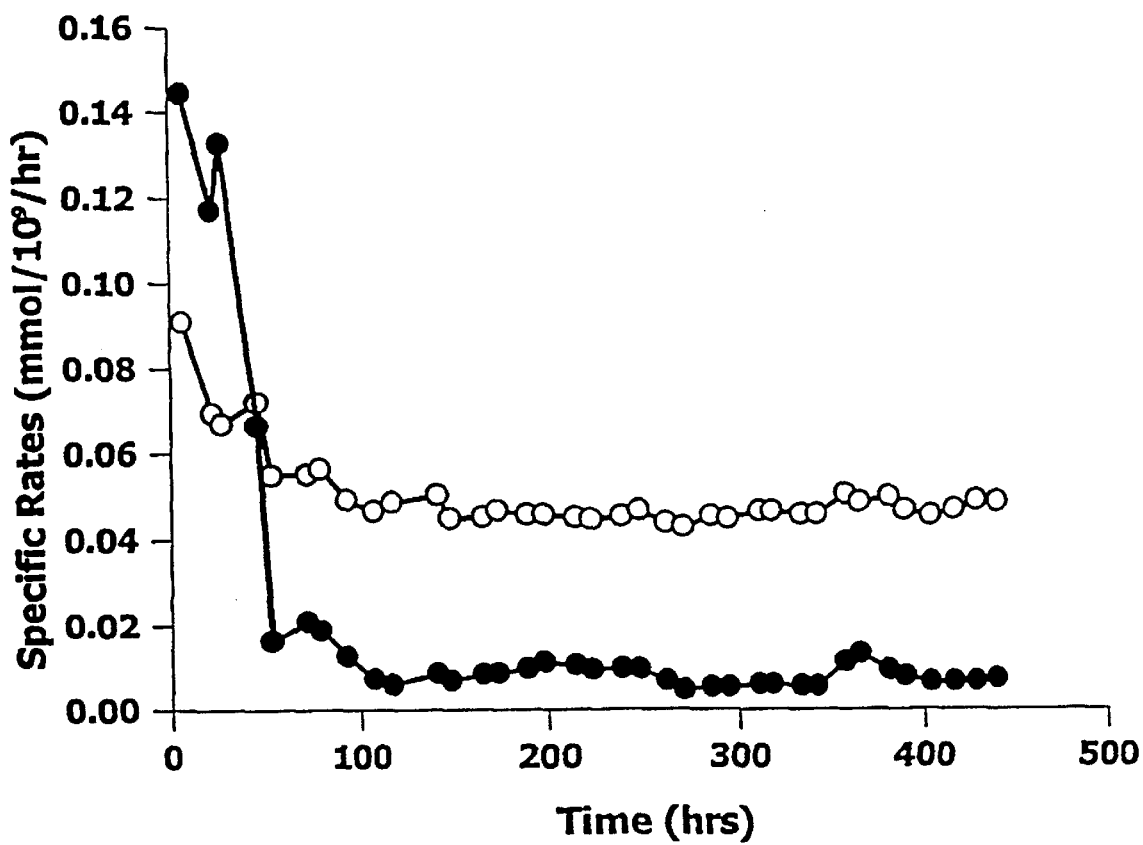
FIG. 14. Specific rates of glucose consumption (filled circles) and lactate production (open circles) in high density continuous culture of hybridoma cells according to the invention (Example 3).
Figure 15:
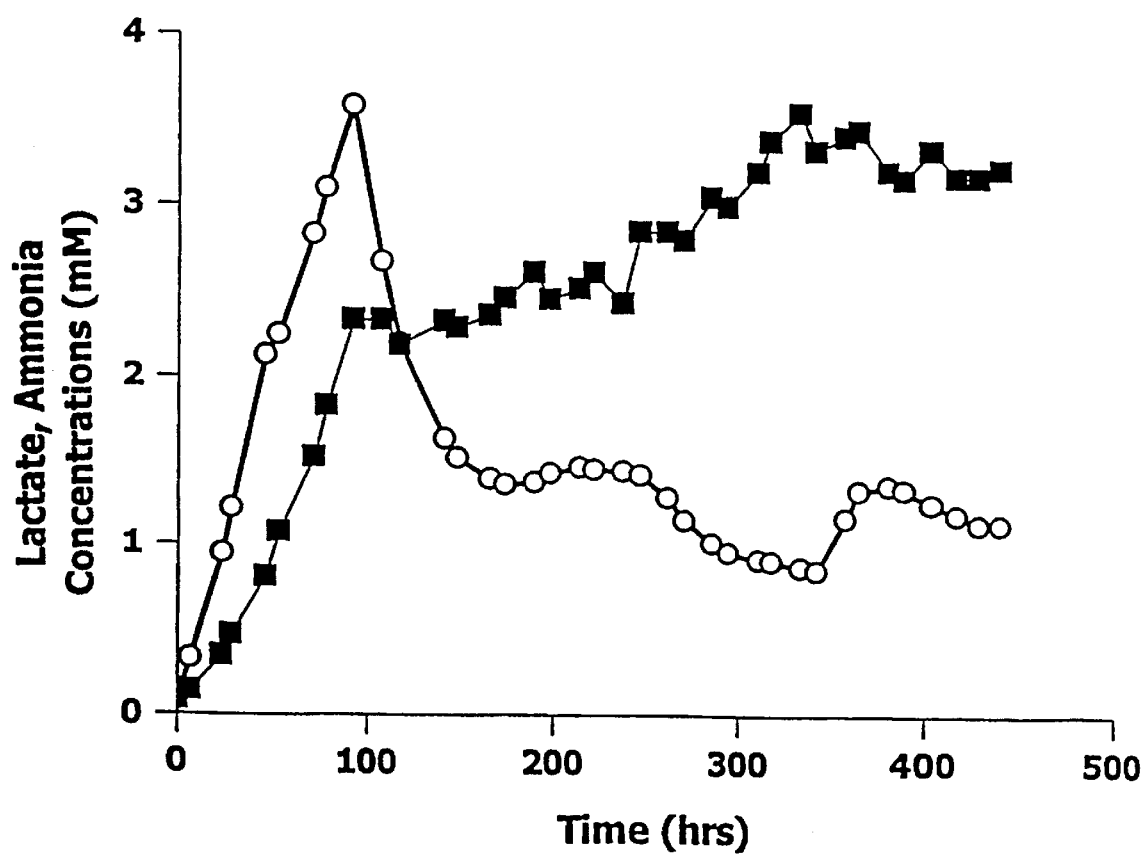
FIG. 15. Lactate (open circles) and ammonia (filled squares) concentrations in high density continuous culture of hybridoma cells according to the invention according to the invention (Example 3).

The viable and total cell concentration profile for the examples is shown in FIG. 12. The glucose and lactate concentrations are shown in FIG. 13 where as their specific rates are shown in FIG. 14. FIG. 15 summarizes the lactate and ammonia concentrations during the culture.

From 10 hours to 93 hours, the culture mode was fed-batch. The online estimation of oxygen consumption rate was used to estimate the amount of feed (described in the section "Hybridoma cell line and culture media") as described in example 2. The cell concentration increased from $0.15 \times 10^6$ viable cells/mL to $3.9 \times 10^6$/mL during this phase, and the viability remained high at about 95%. The stoichiometric ratio of glucose consumption to oxygen consumption, calculated off-line, was adjusted as needed to ensure that the glucose level remain close to set point of 0.28 mM. The ratio changed little after the first few samples, and was then maintained for the duration of the fed-batch phase. At the same time, the specific glucose consumption rate ($q_{glucose}$) and specific lactate production rate ($q_{lactate}$) decreased to 0.05 and 0.015 mmol/$10^9$ cells/hr respectively from 0.09 and 0.1 mmol/$10^9$ cells/hr respectively. At the end of this phase, the lactate concentration in the culture was 3.6 mM (0.32 g/L) and the ammonia concentration was 2.3 mM. The stoichiometric ratio of lactate produced to glucose consumed was about 0.3 mol/mol.

Phase three, representing continuous feeding, started at 93 hours with a dilution rate of 0.03 $hr^{-1}$. The feed contained 6.9 mM (1.24 g/L) of glucose and 4 mM glutamine, with all the other components, except bulk salts, at a concentration 1.9 times that of the basal medium DMEM/F12, with the corresponding increase in concentration of the media additives. At this point, the lactate concentration was 3.6 m (0.32 g/L) and glucose was 0.26 mM (0.046 g/L). After continuous flow started, the viable cell concentration settled to a steady state value of $4.3 \times 10^6$/mL. The steady state lactate concentration was 1.4 mM (0.13 g/L) while the glucose concentration was 0.22 mM (0.04 g/L). The ammonia concentration was 2.3 mM. The specific glucose consumption and lactate production rates were 0.045 and 0.009 mmol/$10^9$ cells/hr. The lactate to glucose molar stoichiometric ratio was 0.2 mol/mol.

At 174 hours, the amino acids in the feed were increased to 2.2 times that of the basal medium DMEM/F12. The rest of the feed was identical to the one used in phase three. This is represented as phase four of the culture and it continued till 246 hours. The cell, glucose and lactate concentrations were $4.3 \times 10^6$ cells/mL, 0.22 mM (0.040 g/L) and 1.4 mM (0.13 g/L): the same as phase three of the culture. The ammonia concentration increased slightly to 2.5 mM. The lactate to glucose molar stoichiometric ratio also remained the same at 0.2 mol/mol. Thus and increase in amino acids did not result in any change in steady state cell concentration or the metabolism of the cells.

From 247 hours to 341 hours, phase five of the culture, the Glutamine in the feed was increased to 4.5 mM. The other components were the same as the feed in phase four. The cell and lactate concentration remained constant at $4.3 \times 10^6$ cells/mL and 0.22 mM (0.04 g/L) while the lactate concentration dropped to 0.83 mM (0.075 g/L). The ammonia concentration increased to 3.3 mM. The specific lactate production rate dropped to 0.005 mmol/$10^9$ cells/hr while the specific glucose consumption rate remained the same. The lactate to glucose molar stoichiometric ratio dropped to 0.11 mol/mol.

Phase six of the culture was initiated at 342 hours when the glucose in the feed was increased to 7.8 mM (1.4 g/L). This resulted in an increase in the cell concentration to $4.7 \times 10^6$ cells/mL. The steady state glucose, lactate and ammonia concentrations were 0.19 mM (0.035 g/L), 1.11 mM (0.1 g/L) and 3.1 mM. The specific lactate production rate increased to 0.007 mmol/$10^9$ cells/hr while the specific glucose consumption rate again remained the same. The stoichiometric molar ratio of lactate to glucose was 0.14 mol/mol. Thus the cell concentration can be increased in continuous cultures of hybridoma cells by increase the nutrients in the feed while properly manipulation the cell metabolism.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variation obvious to one skilled in the art will be included within the invention defined by the claims.

What is claimed is:

1. A method for culturing cells in a suspension state comprising:
   (a) periodically or continuously delivering to a batch cell culture a first nutrient solution comprising glucose in a concentration effective to yield a fed-batch cell culture having a molar stoichiometric ratio of lactate produced to glucose consumed of less than about 1;
   (b) converting the fed-batch cell culture to a continuous cell culture; and
   (c) continuously delivering to the continuous cell culture a second nutrient solution comprising glucose in a concentration effective to maintain a molar stoichiometric ratio of lactate produced to glucose consumed of less than about 1 in the continuous cell culture.

2. The method of claim 1 wherein the first nutrient solution comprises glucose in a concentration effective to yield a fed-batch cell culture wherein molar stoichiometric ratio of lactate produced to glucose consumed is less than about 0.8.

3. The method of claim 1 wherein the first nutrient solution comprises glucose in a concentration effective to yield a fed-batch cell culture wherein molar stoichiometric ratio of lactate produced to glucose consumed is less than about 0.5.

4. The method of claim 3 wherein the second nutrient solution comprises glucose in a concentration effective to maintain molar stoichiometric ratio of lactate produced to glucose consumed at less than about 0.5 in the continuous cell culture.

5. The method of claim 1 wherein the first nutrient solution comprises glucose in a concentration effective to yield a fed-batch cell culture wherein molar stoichiometric ratio of lactate produced to glucose consumed is less than about 0.1.

6. The method of claim 5 wherein the second nutrient solution comprises glucose in a concentration effective to maintain molar stoichiometric ratio of lactate produced to glucose consumed at less than about 0.5 in the continuous cell culture.

7. The method of claim 5 wherein the second nutrient solution comprises glucose in a concentration effective to maintain molar stoichiometric ratio of lactate produced to glucose consumed at less than about 0.1 in the continuous cell culture.

8. The method of claim 1 wherein the glucose concentration in the first nutrient solution is about 22 mM to about 67 mM.

9. The method of claim 1 wherein the first nutrient solution further comprises about 1 mM to about 40 mM glutamine.

10. The method of claim 1 wherein the first nutrient solution is a concentrated nutrient solution comprising glucose, glutamine, and amino acids in amounts and proportions according to a stoichiometric coefficient, step (a) of said method further comprising periodically (i) measuring the glucose concentration in the fed-batch cell culture; (ii) measuring the oxygen consumption of the fed-batch cell culture; (iii) calculating the stoichiometric ratio of glucose in the fed-batch cell culture to oxygen consumption; and (iv) adjusting the feeding rate of the nutrient solution according to the stoichiometric ratio calculated in step (iii) so as to maintain the glucose concentration in the fed-batch cell culture of about 0.05 to about 0.4 mM.

11. The method of claim 1 wherein the first nutrient solution is delivered to the batch culture for a period of about 50 hours to about 100 hours prior to step (b).

12. The method of claim 1 wherein the glucose concentration in the second nutrient solution is about 5 mM to about 25 mM.

13. The method of claim 1 wherein the second nutrient solution further comprises glutamine in a concentration effective to maintain a molar stoichiometric ratio of ammonia produced to glutamine consumed of less than about 1.3.

14. The method of claim 13 wherein the glutamine concentration in the second nutrient solution is about 1 to about 40 mM.

15. The method of claim 1 wherein the second nutrient solution further comprises at least one amino acid, said method further comprising, as step (d), at least one of the steps selected from the group consisting of:
   (i) increasing the concentration of an amino acid in the second nutrient solution;
   (ii) increasing the dilution rate; and
   (iii) increasing the glucose concentration in the second nutrient solution.

16. The method of claim 1 wherein the glucose concentration in the continuous cell culture is maintained at a level of between about 0.05 mM and about 0.4 mM.

17. The method of claim 1 wherein the glutamine concentration in the continuous cell culture is maintained at a level of less than about 0.1 mM.

18. The method of claim 1 wherein the lactate concentration in the continuous cell culture is maintained at a level of less than about 30 mM.

19. The method of claim 1 wherein the lactate concentration in the continuous cell culture is maintained at a level of less than about 5 mM.

20. The method of claim 1 wherein the continuous cell culture is maintained for a period of at least about 300 hours.

21. The method of claim 20 wherein the continuous cell culture is maintained for a period of at least about 1300 hours.

22. The method of claim 1 wherein the viability of the continuous cell culture is maintained at a level of at least about 50%.

23. The method of claim 22 wherein the viability of the continuous cell culture is maintained at a level of at least about 80%.

24. The method of claim 1 wherein a cell density of at least about $4\times10^6$ viable cells/mL is maintained in the continuous cell culture.

25. The method of claim 1 wherein step (c) further comprises continuously harvesting cells from the continuous cell culture.

26. The method of claim 1 wherein the cells produce a product, and wherein step (c) further comprises continuously removing the product from the continuous cell culture.

27. The method of claim 1 performed in a bioreactor.

28. The method of claim 1 wherein the cells are vertebrate cells.

29. The method of claim 28 wherein the cells are mammalian cells.

30. A method for culturing cells in a suspension state comprising:
(a) providing a metabolically-shifted fed-batch cell culture characterized by a molar stoichiometric ratio of lactate produced to glucose consumed of less than about 1;
(b) converting the metabolically-shifted fed-batch culture to a metabolically-shifted continuous cell culture; and
(c) maintaining the cells of the continuous cell culture in a metabolically-shifted state characterized by a stoichiometric molar ratio of lactate produced to glucose consumed of less than about 1.

31. The method of claim 30 wherein the fed-batch culture is characterized by molar stoichiometric ratio of lactate produced to glucose consumed of less than about 0.1.

32. The method of claim 31 wherein molar stoichiometric ratio of lactate produced to glucose consumed for the continuous cell culture is maintained at a level of less than about 0.1.

33. The method of claim 30 wherein the glucose concentration in the continuous cell culture is maintained at a level of between about 0.05 mM and about 0.4 mM.

34. The method of claim 30 wherein the glutamine concentration in the continuous cell culture is maintained at a level of less than about 0.1 mM.

35. The method of claim 30 wherein the lactate concentration in the continuous cell culture is maintained at a level of less than about 30 mM.

36. The method of claim 35 wherein the lactate concentration in the continuous cell culture is maintained at a level of less than about 5 mM.

37. The method of claim 30 wherein the continuous cell culture is maintained for a period of at least about 1300 hours.

38. The method of claim 30 wherein the viability of the continuous cell culture is maintained at a level of at least about 80%.

39. The method of claim 30 wherein a cell density of at least about $4\times10^6$ viable cells/mL is maintained in the continuous cell culture.

40. The method of claim 30 wherein step (c) further comprises continuously harvesting cells from the continuous cell culture.

41. The method of claim 30 wherein the cells produce a product, and wherein step (c) further comprises continuously removing the produce from the continuous cell culture.

42. The method of claim 30 wherein the cells are vertebrate cells.

43. The method of claim 42 wherein the cells are mammalian cells.

44. In a bioreactor for continuous culture of cells, comprising a container, an inlet for delivery of a nutrient feed into the container, an outlet for removal of components of the continuous cell culture from the container, means for measuring the specific consumption rate for glucose, and means for measuring the specific production rate for lactate, the improvement comprising:
a metabolically-shifted continuous culture of cells disposed inside the container characterized by a stoichiometric ratio of lactate produced to glucose consumed of less than about 1.

45. The bioreactor of claim 44 wherein the stoichiometric ratio of lactate produced to glucose consumed is less than about 0.1.

46. The bioreactor of claim 44 which is a chemostat.

* * * * *

UNITED STATES PATENT AND TRADEMARK OFFICE
CERTIFICATE OF CORRECTION

PATENT NO.    : 6,156,570
DATED         : December 5, 2000
INVENTOR(S)   : Hu et al.

It is certified that error appears in the above-identified patent and that said Letters Patent is hereby corrected as shown below:

<u>Title page,</u>
Item [75], Inventors, delete "Wei-Shou Hu, Falcon Heights; Anna F. Europa, Minneapolis, both of Minn." and replace with -- Wei-Shou Hu, Falcon Heights, Minn.; Anna F. Europa, Diliman Quezon City, Philippines --.
Item [57], ABSTRACT,
Line 1, after "A method for cultivating" insert -- mammalian --.

<u>Column 18,</u>
Line 11, after "The method of claim" delete "5" and insert -- 6 -- therefor.
Line 65, after "The method of claim" delete "1" and insert -- 18 -- therefor.

<u>Column 20,</u>
Line 25, after "removing the" delete "produce" and insert -- product -- therefor.

Signed and Sealed this

Twelfth Day of November, 2002

Attest:

JAMES E. ROGAN
Attesting Officer    Director of the United States Patent and Trademark Office